(12) United States Patent
Maes et al.

(10) Patent No.: US 9,782,335 B2
(45) Date of Patent: Oct. 10, 2017

(54) MALIC ACID ESTERS OF RESVERATROL AND COSMETIC COMPOSITIONS

(71) Applicant: ELC Management LLC, Melville, NY (US)

(72) Inventors: Daniel H. Maes, Huntington, NY (US); Fatemeh Mohammadi, Hauppauge, NY (US); Lisa Qu, Flushing, NY (US); Anna Czarnota, Commack, NY (US); Thomas Mammone, Farmingdale, NY (US); Julius R. Zecchino, New York, NY (US); Lieve Declercq, Ekeren (BE)

(73) Assignee: ELC Management LLC, New York, NY (US)

( * ) Notice: Subject to any disclaimer, the term of this patent is extended or adjusted under 35 U.S.C. 154(b) by 18 days.

(21) Appl. No.: 15/133,552

(22) Filed: Apr. 20, 2016

(65) Prior Publication Data
US 2016/0229791 A1 Aug. 11, 2016

Related U.S. Application Data

(63) Continuation of application No. 14/875,858, filed on Oct. 6, 2015, which is a continuation of application No. 13/863,719, filed on Apr. 16, 2013, now Pat. No. 9,162,083, which is a continuation of application No. 13/294,229, filed on Nov. 11, 2011, now Pat. No. 8,461,200, which is a continuation of application No. 12/127,439, filed on May 27, 2008, now Pat. No. 8,080,583.

(60) Provisional application No. 60/952,881, filed on Jul. 31, 2007.

(51) Int. Cl.

| | |
|---|---|
| A61K 31/216 | (2006.01) |
| A61K 8/37 | (2006.01) |
| A61K 8/34 | (2006.01) |
| A61K 8/42 | (2006.01) |
| A61K 8/58 | (2006.01) |
| A61K 8/60 | (2006.01) |
| A61K 31/05 | (2006.01) |
| A61Q 19/00 | (2006.01) |
| A61Q 1/10 | (2006.01) |
| A61Q 1/12 | (2006.01) |
| A61Q 19/08 | (2006.01) |
| A61Q 1/02 | (2006.01) |
| A61Q 1/06 | (2006.01) |
| A61Q 1/08 | (2006.01) |
| A61Q 17/04 | (2006.01) |
| A61K 8/97 | (2017.01) |
| C07C 69/604 | (2006.01) |
| A61K 8/02 | (2006.01) |
| A61K 8/06 | (2006.01) |
| A61K 8/25 | (2006.01) |
| C07C 69/94 | (2006.01) |
| A61K 8/891 | (2006.01) |
| C07C 69/017 | (2006.01) |
| C07C 69/30 | (2006.01) |

(52) U.S. Cl.
CPC ............ *A61K 8/375* (2013.01); *A61K 8/0241* (2013.01); *A61K 8/062* (2013.01); *A61K 8/064* (2013.01); *A61K 8/066* (2013.01); *A61K 8/25* (2013.01); *A61K 8/347* (2013.01); *A61K 8/37* (2013.01); *A61K 8/42* (2013.01); *A61K 8/585* (2013.01); *A61K 8/60* (2013.01); *A61K 8/602* (2013.01); *A61K 8/891* (2013.01); *A61K 8/97* (2013.01); *A61K 31/05* (2013.01); *A61Q 1/02* (2013.01); *A61Q 1/06* (2013.01); *A61Q 1/08* (2013.01); *A61Q 1/10* (2013.01); *A61Q 1/12* (2013.01); *A61Q 17/04* (2013.01); *A61Q 19/00* (2013.01); *A61Q 19/007* (2013.01); *A61Q 19/08* (2013.01); *C07C 69/017* (2013.01); *C07C 69/30* (2013.01); *C07C 69/604* (2013.01); *C07C 69/94* (2013.01); *A61K 2800/31* (2013.01); *A61K 2800/43* (2013.01); *A61K 2800/54* (2013.01); *A61K 2800/591* (2013.01); *A61K 2800/596* (2013.01)

(58) Field of Classification Search
None
See application file for complete search history.

(56) References Cited

U.S. PATENT DOCUMENTS

| | | |
|---|---|---|
| 8,048,456 B2 | 11/2011 | Burke-Colvin et al. |
| 2002/0022040 A1 | 2/2002 | Robinson et al. |
| 2010/0216879 A1 | 8/2010 | Maes et al. |

FOREIGN PATENT DOCUMENTS

| | | |
|---|---|---|
| EP | 0945425 | 9/1999 |
| WO | WO-01/97769 | 12/2001 |
| WO | WO-2004/054533 | 7/2004 |
| WO | WO-2005069998 | * 8/2005 |

OTHER PUBLICATIONS

Supplemental European Search Report; EP08755460.6; Completion Date: May 11, 2015; dated May 15, 2015.
Supplemental European Search Report; EP08829394; Completion Date: Feb. 20, 2015; dated Mar. 2, 2015.

\* cited by examiner

*Primary Examiner* — Abigail Vanhorn
*Assistant Examiner* — Jessica Kassa
(74) *Attorney, Agent, or Firm* — Julie Blackburn

(57) ABSTRACT

Succinic acid esters of resveratrol and topical compositions containing the esters.

18 Claims, No Drawings

MALIC ACID ESTERS OF RESVERATROL AND COSMETIC COMPOSITIONS

TECHNICAL FIELD

The invention is in the field of aqueous based cosmetic compositions, such as emulsions or gels, for application to keratinous surfaces.

BACKGROUND OF THE INVENTION

Resveratrol, also referred to as 3,4',5-trihydroxystilbene is a polyhydroxy-substituted compound having the general formula:

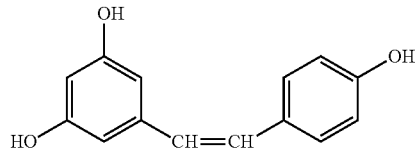

It is present in red grapes, raspberries, blueberries, and certain other plant berries or extracts. It has been reported that resveratrol has anti-aging, anti-cancer, and antiviral effects. Because of its perceived fountain-of-youth properties, resveratrol has been incorporated into a variety of cosmetic formulations such skin creams. However, one problem with resveratrol is that it is generally unstable in cosmetic formulations. Accordingly, if used in cosmetic formulas it can only be used in very small amounts. If present in too large an amount the resveratrol will hydrolyze and cause the cosmetic formulation into which it is incorporated to become discolored.

One way to address the instability of resveratrol is to derivatize the resveratrol by reacting one or more of the hydroxyl groups with substituents that confer stability when the resveratrol is formulated into cosmetic products. It has been discovered that esterifying resveratrol with inorganic acids, organic carboxylic acids, or reacting the hydroxyl groups to form alkoxy substituents or glycosides, provides reservatrol derivatives that are stable in cosmetic emulsions and enable formulation of cosmetic products with the aesthetics and stability that are necessary for commercially successful products. Consumers expect efficacy, fairly immediate visible results, and excellent aesthetics in tactile properties such as application, feel, blendability, and the like. For example, pharmaceutical ointments are carriers for a variety of actives but exhibit a very undesirable aesthetic that the cosmetics consumer would find unacceptable for day to day wear. Derivatizing resveratrol as set forth herein enables the cosmetic formulator to formulate very aesthetically pleasing and stable cosmetic formulations that provide commercially acceptable products for the cosmetics consumer.

It is an object of the invention to provide aqueous based cosmetic compositions containing at least one resveratrol derivative, preferably one that is hydrolytically stable in cosmetic formulations that are aqueous based and provide a light feel and texture when applied to skin.

It is a further object of the invention to provide an aqueous based cosmetic composition containing at least one resveratrol derivative, a water phase, and an oil phase containing at least one linear volatile or linear near volatile silicone.

It is a further object of the invention to provide emulsion skin care compositions in the form of creams, lotions, serums, gels, foundation makeups, mascaras, and the like, containing at least one resveratrol derivative, water, and oil phase containing at least one linear volatile or near volatile silicone.

SUMMARY OF THE INVENTION

The invention is directed to an emulsion cosmetic composition comprising at least one resveratrol derivative, an aqueous phase, and an oil phase containing at least one linear volatile or near volatile silicone, or trisiloxane.

The compositions of the invention provide a light, blendable, aesthetically pleasing texture that dries quickly due, at least in part, to the linear volatile or near volatile silicone oil.

DETAILED DESCRIPTION

The compositions of the invention may be in the water-in-oil or oil-in-water emulsion form. The amount of water may range from about 0.1-99%, preferably from about 5-85%, more preferably from about 7-75% by weight of the total composition. The amount of oil will preferably range from about 1-95%, preferably from about 5-85%, more preferably from about 7-65% by weight of the total composition.

I. Resveratrol Derivatives

Without being bound by this explanation, it is believed that the practical use of resveratrol in cosmetic compositions has been limited by instability due to the phenol groups. The resveratrol derivatives used in the compositions of the invention contain protective groups, which function to stabilize the phenol groups of resveratrol and make the resveratrol derivative suitable for use in emulsions where superior aesthetics and stability are required for commercially acceptable products. In addition, once the compositions containing the derivative is applied to skin, the protective groups can be easily hydrolyzed from the molecule, preferably by enzymes and other ingredients on the skin surface, to release an active form of resveratrol into the skin.

The resveratrol derivatives of the present invention have a general formula of:

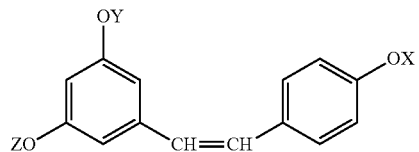

wherein X, Y, and Z are either hydrogen or a protective group, provided that at least one of X, Y, and Z is the protective group.

The resveratrol derivatives may be present ranging from about 0.001 to 95%, preferably from about 0.005 to 90%, more preferably from about 0.1 to 20% by weight of the total composition.

A. Resveratrol Esters of Inorganic or Organic Acids

Resveratrol esters of inorganic acids, in which one or more of the X, Y, and Z are inorganic acid functional groups such as phosphates, nitrates, sulfonates, and carbonates, can be used in the present invention. Following is a list of exemplary inorganic acid esters that are particularly suitable for practice of the present invention:

3-phosphate-5,4'-dihydroxystilbene;
5-phosphate-3,4'-dihydroxystilbene;
4'-phosphate-3,5-dihydroxystilbene;

3,5-diphsophate-4'-hydroxystilbene;
3,4'-diphosphate-5-hydroxystilbene;
4',5-diphosphate-3-hydroxystilbene;
3,5,4'-triphosphate stilbene;
3-nitrate-5,4'-dihydroxystilbene;
5-nitrate-3,4'-dihydroxystilbene;
4'-nitrate-3,5-dihydroxystilbene;
3,5-dinitrate-4'-hydroxystilbene;
3,4'-dinitrate-5-hydroxystilbene;
4',5-dinitrate-3-hydroxystilbene;
3,5,4'-trinitrate stilbene;
3-sulfonate-5,4'-dihydroxystilbene;
5-sulfonate-3,4'-dihydroxystilbene;
4'-sulfonate-3,5-dihydroxystilbene;
3,5-disulfonate-4'-hydroxystilbene;
3,4'-disulfonate-5-hydroxystilbene;
4',5-disulfonate-3-hydroxystilbene;
3,5,4'-trisulfonate stilbene;
3-carbonate-5,4'-dihydroxystilbene;
5-carbonate-3,4'-dihydroxystilbene;
4'-carbonate-3,5-dihydroxystilbene;
3,5-dicarbonate-4'-hydroxystilbene;
3,4'-dicarbonate-5-hydroxystilbene;
4',5-dicarbonate-3-hydroxystilbene; and
3,5,4'-tricarbonate stilbene.

Pharmaceutically acceptable salts of the above-listed resveratrol esters can also be used in the cosmetic compositions of the present invention. Such salts may include one or more monovalent or divalent cations selected from the group consisting of Na, K, Mg, Ca, Fe, and $NH_4$. The salts can be formed by adding corresponding bases, such as sodium hydroxide, potassium hydroxide, and the like, into a solution containing the resveratrol esters.

Such inorganic acid esters of resveratrol may be readily formed by well known chemical processes that substitute the hydroxyl groups of phenols or polyphenols with the phosphate, sulfonates, and carbonate functional groups. For example, U.S. Pat. No. 4,003,966 describes a one-step process for selectively phosphorylating phenols to form phosphate esters thereof, which is hereby incorporated herein by reference in its entirety for all purposes.

Preferred is the 3,4',5-triphosphate stilbene, also referred to as a resveratrol triphosphate ester having the formula (resveratrol triphosphate):

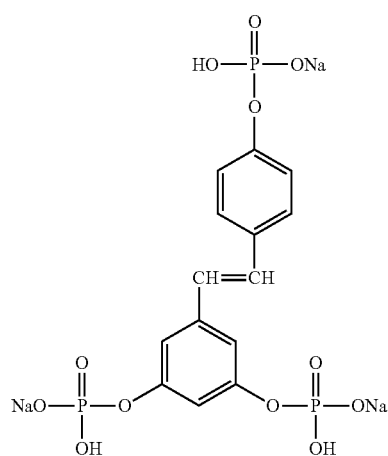

Phosphate esters of resveratrol, including resveratrol triphosphate, are disclosed in International Patent Application Publication No. WO 2006/029484A1, which is hereby incorporated by reference in its entirety. Resveratrol triphosphate may be synthesized by the method as set forth in Example 2 of WO 2006/029484A1. More specifically, a solution of resveratrol (3,4,5-trihydroxystilbene) (25 mmols, 5.7 grams) and dimethylaminopyridine (7.5 mmols, 0.93 grams) in 100 ml acetonitrile is cooled under nitrogen up to −10° C. After 10 minutes, carbon tetrachloride (375 mmol, 36.2 ml) and DIEA (159 mmol; 27.7 ml) and the mixture maintained under stirring for 30 minutes. Dibenzylphosphate (113 mmols, 25.0 ml) is added and the mixture stirred for an additional 12 hours at room temperature. The course of the reaction is monitored by TLC (silica F254, eluent ethyl acetate/n-hexane 80/20 v/v). One liter of 0.5 M $KH_2PO_4$ is added, and the mixture then extract with ethyl acetate. The resulting product, tri(dibenzylphosphate) resveratrol, is purified by filtration on a silica gel, washing first with a mixture of ethyl acetate/n-hexane (80/20 v/v) to remove any remaining unreacted resveratrol, and then with methanol, to obtain a yellow oil.

To the tri(dibenzylphosphate) resveratrol (12.5 mmol) in 200 mL of anhydrous DCM at 0° C., is added bromomethylsilane (79 mmols, 10.4 mL). After 2 hours, 300 mL of $H_2O$ is added, and the reaction mixture is stirred for 1 hour. The water phase is washed again with ethyl acetate, then lyophilized to obtain an orange oil.

To the product obtained above, solubilized in 400 mL of ethanol, is added $CH_3ONa$ (37 mmol; 2.03 g) and the reaction stirred for 12 hours at room temperature. The ethanol is evaporated in a rotavapor, and the residue solubilized in $H_2O$. The water phase is washed with ethyl acetate and lyophilized. The mass spectrum of the resulting white solid shows the presence of resveratrol triphosphate (PM=468.1), with a total yield of >90% with respect to resveratrol.

If desired the resveratrol triphosphate may be neutralized with organic or inorganic bases such as sodium hydroxide, potassium hydroxide and the like. Particularly preferred is where the resveratrol triphosphate is neutralized with sodium hydroxide to form trisodium resveratrol triphosphate.

B. Carboxylic Acid Esters of Resveratrol

Another group of resveratrol derivatives that can be used in the present invention is esters of resveratrol and carboxylic acids, in which one or more of X, Y, and Z is a —C(O)—$R_1$ group, wherein $R_1$ is selected from the group consisting of linear, branched or cyclic $C_1$-$C_{40}$ alkyl, substituted $C_1$-$C_{40}$ alkyl, $C_1$-$C_{40}$ alkenyl, substituted $C_1$-$C_{40}$ alkenyl, $C_1$-$C_{40}$ alkynyl, substituted $C_1$-$C_{40}$alkynyl, $C_1$-$C_{40}$ aryl, and $C_1$-$C_{40}$ substituted aryl. In one preferred embodiment, the R group is a straight or branched chain fatty, or $C_{6-30}$, saturated or unsaturated alkyl group.

Exemplary carboxylic acids that can be used to form ester of resveratrol include, but are not limited to: substituted or unsubstituted saturated monocarboxylic acids, such as acetic acid, propionic acid, butyric acid (C4), valeric acid, hexanoic acid, caprylic acid (C8), lauric acid, stearic acid (C18), isostearic acid (branched C18), linoleic acid, linolenic acid, myristic acid (C14), arachidic acid (C20), arichidonic acid, erucic acid, behenic acid (C22), lauric acid (C12), capric acid (C10), caproic (C6), and palmitic acid (C16); unsaturated monocarboxylic acids, such as acrylic acid, methacrylic acid, sorbic acid, oleic acid, linoleic acid, linolenic acid, docosahexaenoic acid, and eicosapentaenoic acid; or carboxylic acids substituted with cyclic disulfide groups, e.g. lipoic acid; amino acids, such as arginine, glutamine, and tyrosine; keto acids, such as pyruvic acid and acetoacetic acid; aromatic carboxylic acids, such as ascorbic acid, benzoic acid, salicylic acid, and ferulic acid; di- and tri-carboxylic acids, such as oxalic acid, malonic acid, malic acid, succinic acid, and glutaric acid. The designation "C" followed by a number indicates the number of carbon atoms in the alkyl chain.

Following is a list of exemplary carboxylic acid esters of resveratrol that are particularly suitable for practice of the present invention:

3-acetate-5,4'-dihydroxystilbene;
5-acetate-3,4'-dihydroxystilbene;
4'-acetate-3,5-dihydroxystilbene;
3,5-diacetate-4'-hydroxystilbene;
3,4'-diacetate-5-hydroxystilbene;
4',5-diacetate-3-hydroxystilbene;
3,5,4'-triacetate stilbene;
3-propionate-5,4'-dihydroxystilbene;
5-propionate-3,4'-dihydroxystilbene;
4'-propionate-3,5-dihydroxystilbene;
3,5-dipropionate-4'-hydroxystilbene;
3,4'-dipropionate-5-hydroxystilbene;
4',5-dipropionate-3-hydroxystilbene;
3,5,4'-tripropionate stilbene;
3-butyrate-5,4'-dihydroxystilbene;
5-butyrate-3,4'-dihydroxystilbene;
4'-butyrate-3,5-dihydroxystilbene;
3,5-dibutyrate-4'-hydroxystilbene;
3,4'-dibutyrate-5-hydroxystilbene;
4',5-dibutyrate-3-hydroxystilbene;
3,5,4'-tributyrate stilbene;
3-valerate-5,4'-dihydroxystilbene;
5-valerate-3,4'-dihydroxystilbene;
4'-valerate-3,5-dihydroxystilbene;
3,5-divalerate-4'-hydroxystilbene;
3,4'-divalerate-5-hydroxystilbene;
4',5-divalerate-3-hydroxystilbene;
3,5,4'-trivalerate stilbene;
3-hexanoate-5,4'-dihydroxystilbene;
5-hexanoate-3,4'-dihydroxystilbene;
4'-hexanoate-3,5-dihydroxystilbene;
3,5-dihexanoate-4'-hydroxystilbene;
3,4'-dihexanoate-5-hydroxystilbene;
4',5-dihexanoate-3-hydroxystilbene;
3,5,4'-trihexanoate stilbene;
3-caprylate-5,4'-dihydroxystilbene;
5-caprylate-3,4'-dihydroxystilbene;
4'-caprylate-3,5-dihydroxystilbene;
3,5-dicaprylate-4'-hydroxystilbene;
3,4'-dicaprylate-5-hydroxystilbene;
4',5-dicaprylate-3-hydroxystilbene;
3,5,4'-tricaprylate stilbene;
3-laurate-5,4'-dihydroxystilbene;
5-laurate-3,4'-dihydroxystilbene;
4'-laurate-3,5-dihydroxystilbene;
3,5-dilaurate-4'-hydroxystilbene;
3,4'-dilaurate-5-hydroxystilbene;
4',5-dilaurate-3-hydroxystilbene;
3,5,4'-trilaurate stilbene;
3-stearate-5,4'-dihydroxystilbene;
5-stearate-3,4'-dihydroxystilbene;
4'-stearate-3,5-dihydroxystilbene;
3,5-distearate-4'-hydroxystilbene;
3,4'-distearate-5-hydroxystilbene;
4',5-distearate-3-hydroxystilbene;
3,5,4'-tristearate stilbene;
3-palmitate-5,4'-dihydroxystilbene;
5-palmitate-3,4'-dihydroxystilbene;
4'-palmitate-3,5-dihydroxystilbene;
3,5-dipalmitate-4'-hydroxystilbene;
3,4'-dipalmitate-5-hydroxystilbene;
4',5-dipalmitate-3-hydroxystilbene;
3,5,4'-tripalmitate stilbene;
3-acrylate-5,4'-dihydroxystilbene;
5-acrylate-3,4'-dihydroxystilbene;
4'-acrylate-3,5-dihydroxystilbene;
3,5-diacrylate-4'-hydroxystilbene;
3,4'-diacrylate-5-hydroxystilbene;
4',5-diacrylate-3-hydroxystilbene;
3,5,4'-triacrylate stilbene;
3-methacrylate-5,4'-dihydroxystilbene;
5-methacrylate-3,4'-dihydroxystilbene;
4'-methacrylate-3,5-dihydroxystilbene;
3,5-dimethacrylate-4'-hydroxystilbene;
3,4'-dimethacrylate-5-hydroxystilbene;
4',5-dimethacrylate-3-hydroxystilbene;
3,5,4'-trimethacrylate stilbene;
3-sorbate-5,4'-dihydroxystilbene;
5-sorbate-3,4'-dihydroxystilbene;
4'-sorbate-3,5-dihydroxystilbene;
3,5-disorbate-4'-hydroxystilbene;
3,4'-disorbate-5-hydroxystilbene;
4',5-disorbate-3-hydroxystilbene;
3,5,4'-trisorbate stilbene;
3-oleate-5,4'-dihydroxystilbene;
5-oleate-3,4'-dihydroxystilbene;
4'-oleate-3,5-dihydroxystilbene;
3,5-dioleate-4'-hydroxystilbene;
3,4'-dioleate-5-hydroxystilbene;
4',5-dioleate-3-hydroxystilbene;
3,5,4'-trioleate stilbene;
3-linoleate-5,4'-dihydroxystilbene;
5-linoleate-3,4'-dihydroxystilbene;
4'-linoleate-3,5-dihydroxystilbene;
3,5-dilinoleate-4'-hydroxystilbene;
3,4'-dilinoleate-5-hydroxystilbene;
4',5-dilinoleate-3-hydroxystilbene;
3,5,4'-trilinoleate stilbene;
3-linolenate-5,4'-dihydroxystilbene;
5-linolenate-3,4'-dihydroxystilbene;
4'-linolenate-3,5-dihydroxystilbene;
3,5-dilinolenate-4'-hydroxystilbene;
3,4'-dilinolenate-5-hydroxystilbene;
4',5-dilinolenate-3-hydroxystilbene;
3,5,4'-trilinolenate stilbene;
3-docosahexaenoate-5,4'-dihydroxystilbene;
5-docosahexaenoate-3,4'-dihydroxystilbene;
4'-docosahexaenoate-3,5-dihydroxystilbene;
3,5-didocosahexaenoate-4'-hydroxystilbene;
3,4'-didocosahexaenoate-5-hydroxystilbene;
4',5-didocosahexaenoate-3-hydroxystilbene;
3,5,4'-tridocosahexaenoate stilbene;
3-eicosapentaenoic-5,4'-dihydroxystilbene;
5-eicosapentaenoic-3,4'-dihydroxystilbene;
4'-eicosapentaenoic-3,5-dihydroxystilbene;
3,5-dieicosapentaenoic-4'-hydroxystilbene;
3,4'-dieicosapentaenoic-5-hydroxystilbene;
4',5-dieicosapentaenoic-3-hydroxystilbene;
3,5,4'-trieicosapentaenoic stilbene;
3-arginate-5,4'-dihydroxystilbene;
5-arginate-3,4'-dihydroxystilbene;
4'-arginate-3,5-dihydroxystilbene;
3,5-diarginate-4'-hydroxystilbene;
3,4'-diarginate-5-hydroxystilbene;
4',5-diarginate-3-hydroxystilbene;

3,5,4'-triarginate stilbene;
3-glutamate-5,4'-dihydroxystilbene;
5-glutamate-3,4'-dihydroxystilbene;
4'-glutamate-3,5-dihydroxystilbene;
3,5-diglutamate-4'-hydroxystilbene;
3,4'-diglutamate-5-hydroxystilbene;
4',5-diglutamate-3-hydroxystilbene;
3,5,4'-triglutamate stilbene;
3-tyrosate-5,4'-dihydroxystilbene;
5-tyrosate-3,4'-dihydroxystilbene;
4'-tyrosate-3,5-dihydroxystilbene;
3,5-dityrosate-4'-hydroxystilbene;
3,4'-dityrosate-5-hydroxystilbene;
4',5-dityrosate-3-hydroxystilbene;
3,5,4'-trityrosate stilbene;
3-pyruvate-5,4'-dihydroxystilbene;
5-pyruvate-3,4'-dihydroxystilbene;
4'-pyruvate-3,5-dihydroxystilbene;
3,5-dipyruvate-4'-hydroxystilbene;
3,4'-dipyruvate-5-hydroxystilbene;
4',5-dipyruvate-3-hydroxystilbene;
3,5,4'-tripyruvate stilbene;
3-acetoacetate-5,4'-dihydroxystilbene;
5-acetoacetate-3,4'-dihydroxystilbene;
4'-acetoacetate-3,5-dihydroxystilbene;
3,5-diacetoacetate-4'-hydroxystilbene;
3,4'-diacetoacetate-5-hydroxystilbene;
4',5-diacetoacetate-3-hydroxystilbene;
3,5,4'-triacetoacetate stilbene;
3-ascorbate-5,4'-dihydroxystilbene;
5-ascorbate-3,4'-dihydroxystilbene;
4'-ascorbate-3,5-dihydroxystilbene;
3,5-diascorbate-4'-hydroxystilbene;
3,4'-diascorbate-5-hydroxystilbene;
4',5-diascorbate-3-hydroxystilbene;
3,5,4'-triascorbate stilbene;
3-benzoate-5,4'-dihydroxystilbene;
5-benzoate-3,4'-dihydroxystilbene;
4'-benzoate-3,5-dihydroxystilbene;
3,5-dibenzoate-4'-hydroxystilbene;
3,4'-dibenzoate-5-hydroxystilbene;
4',5-dibenzoate-3-hydroxystilbene;
3,5,4'-tribenzoate stilbene;
3-salicylate-5,4'-dihydroxystilbene;
5-salicylate-3,4'-dihydroxystilbene;
4'-salicylate-3,5-dihydroxystilbene;
3,5-disalicylate-4'-hydroxystilbene;
3,4'-disalicylate-5-hydroxystilbene;
4',5-disalicylate-3-hydroxystilbene;
3,5,4'-trisalicylate stilbene;
3-ferulate-5,4'-dihydroxystilbene;
5-ferulate-3,4'-dihydroxystilbene;
4'-ferulate-3,5-dihydroxystilbene;
3,5-diferulate-4'-hydroxystilbene;
3,4'-diferulate-5-hydroxystilbene;
4',5-diferulate-3-hydroxystilbene;
3,5,4'-triferulate stilbene;
3-oxalate-5,4'-dihydroxystilbene;
5-oxalate-3,4'-dihydroxystilbene;
4'-oxalate-3,5-dihydroxystilbene;
3,5-dioxalate-4'-hydroxystilbene;
3,4'-dioxalate-5-hydroxystilbene;
4',5-dioxalate-3-hydroxystilbene;
3,5,4'-trioxalate stilbene;
3-malonate-5,4'-dihydroxystilbene;
5-malonate-3,4'-dihydroxystilbene;
4'-malonate-3,5-dihydroxystilbene;
3,5-dimalonate-4'-hydroxystilbene;
3,4'-dimalonate-5-hydroxystilbene;
4',5-dimalonate-3-hydroxystilbene;
3,5,4'-trimalonate stilbene;
3-malate-5,4'-dihydroxystilbene;
5-malate-3,4'-dihydroxystilbene;
4'-malate-3,5-dihydroxystilbene;
3,5-dimalate-4'-hydroxystilbene;
3,4'-dimalate-5-hydroxystilbene;
4',5-dimalate-3-hydroxystilbene;
3,5,4'-trimalate stilbene;
3-succinate-5,4'-dihydroxystilbene;
5-succinate-3,4'-dihydroxystilbene;
4'-succinate-3,5-dihydroxystilbene;
3,5-disuccinate-4'-hydroxystilbene;
3,4'-disuccinate-5-hydroxystilbene;
4',5-disuccinate-3-hydroxystilbene;
3,5,4'-trisuccinate stilbene;
3-glutarate-5,4'-dihydroxystilbene;
5-glutarate-3,4'-dihydroxystilbene;
4'-glutarate-3,5-dihydroxystilbene;
3,5-diglutarate-4'-hydroxystilbene;
3,4'-diglutarate-5-hydroxystilbene;
4',5-diglutarate-3-hydroxystilbene;
3,5,4'-triglutarate stilbene;
3-glutarate-5,4'-dihydroxystilbene;
5-glutarate-3,4'-dihydroxystilbene;
4'-glutarate-3,5-dihydroxystilbene;
3,5-diglutarate-4'-hydroxystilbene;
3,4'-diglutarate-5-hydroxystilbene;
4',5-diglutarate-3-hydroxystilbene; and
3,5,4'-triglutarate stilbene;

One particularly preferred group of carboxylic acid esters of resveratrol are either saturated or unsaturated fatty acid esters of resveratrol, such as resveratrol butyrates, resveratrol valerates, resveratrol hexanoates, resveratrol sorbates, resveratraol laurates, resveratrol stearates, resveratrol palmitates, resveratrol oleates, resveratrol linoleates, resveratrol linolenates, resveratrol eicosapentaenoates, resveratrol lipoates, and resveratrol docosahexanoates. Such fatty acid esters of resveratrol can be readily formed by esterification of resveratrol with acid derivaties according to the Schotten-Baumann reaction in alkaline aqueous medium, as described by U.S. Pat. No. 6,572,882, the content of which is incorporated herein by reference in its entireties for all purposes.

Another particularly preferred group of carboxylic acid esters of resveratrol are the aromatic carboxylic acid esters of resveratrol, such as resveratrol ferulates, which can be formed by simply combining ferulic acid with resveratrol in an aqueous medium.

C. Resveratrol Ether Derivatives

Yet another group of resveratrol derivatives that can be used in the present invention are resveratrol ethers, in which one or more of X, Y, and Z is —$R_2$, wherein $R_2$ is selected from the group consisting of linear, branched or cyclic $C_1$-$C_{40}$ alkyl, substituted $C_1$-$C_{40}$ alkyl, $C_1$-$C_{40}$ alkenyl, substituted $C_1$-$C_{40}$ alkenyl, $C_1$-$C_{40}$ alkynyl, substituted $C_1$-$C_{40}$ alkynyl, $C_1$-$C_{40}$ aryl, substituted $C_1$-$C_{40}$ aryl, and mono-, di-, oligo-, and polysaccharides. Following is a list of exemplary resveratrol ethers that are particularly suitable for practice of the present invention:
3-methoxy-5,4'-dihydroxystilbene;
5-methoxy-3,4'-dihydroxystilbene;
4'-methoxy-3,5-dihydroxystilbene;
3,5-dimethoxy-4'-hydroxystilbene;
3,4'-dimethoxy-5-hydroxystilbene;
4',5-dimethoxy-3-hydroxystilbene;

3,5,4'-trimethoxy stilbene;
3-ethoxy-5,4'-dihydroxystilbene;
5-ethoxy-3,4'-dihydroxystilbene;
4'-ethoxy-3,5-dihydroxystilbene;
3,5-diethoxy-4'-hydroxystilbene;
3,4'-diethoxy-5-hydroxystilbene;
4',5-diethoxy-3-hydroxystilbene;
3,5,4'-triethoxy stilbene;
3-propyloxy-5,4'-dihydroxystilbene;
5-propyloxy-3,4'-dihydroxystilbene;
4'-propyloxy-3,5-dihydroxystilbene;
3,5-dipropyloxy-4'-hydroxystilbene;
3,4'-dipropyloxy-5-hydroxystilbene;
4',5-dipropyloxy-3-hydroxystilbene;
3,5,4'-tripropyloxy stilbene;
3-phenyloxy-5,4'-dihydroxystilbene;
5-phenyloxy-3,4'-dihydroxystilbene;
4'-phenyloxy-3,5-dihydroxystilbene;
3,5-diphenyloxy-4'-hydroxystilbene;
3,4'-diphenyloxy-5-hydroxystilbene;
4',5-diphenyloxy-3-hydroxystilbene;
3,5,4'-triphenyloxy stilbene;
3-glucoside-5,4'-dihydroxystilbene;
5-glucoside-3,4'-dihydroxystilbene;
4'-glucoside-3,5-dihydroxystilbene;
3,5-diglucoside-4'-hydroxystilbene;
3,4'-diglucoside-5-hydroxystilbene;
4',5-diglucoside-3-hydroxystilbene; and
3,5,4'-triglucoside stilbene.

In one specific embodiment of the present invention, a methoxy-substituted resveratrol derivative is used. For example, the compositions of the present invention may comprise 3,5-dimethoxy-4'-hydroxystilbene, which can be extracted from the Indian Kino Tree (*Pterocarpus marsupium*) and is commercially available under the trade name "Pterostilbene" from Sigma-Aldrich at St. Louis, Mo.

In another specific embodiment of the present invention, the resveratrol derivative contains one or more saccharide-containing protective groups, such as glucose, galactose, mannose, fructose, sucrose, lactose, maltose, trehalose, and the like. For example, resveratrol glucoside, which can be obtained by extraction from plants or plant material such as *polygonum cuspidatum* tissue or in vitro cultures of *vitis vinifera* cells, is used in the cosmetic compositions of the present invention.

D. Nitrogen-Containing Derivatives of Resveratrol

The resveratrol derivatives used in the compositions of the present invention may also contain one or more nitrogen-containing functional groups, i.e., one or more of X, Y, and Z in the above formula are selected from the group consisting of amides, amines, imines, amidines, and carboxamidines. Following is a list of exemplary resveratrol ethers that are particularly suitable for practice of the present invention:
3-amide-5,4'-dihydroxystilbene;
5-amide-3,4'-dihydroxystilbene;
4'-amide-3,5-dihydroxystilbene;
3,5-diamide-4'-hydroxystilbene;
3,4'-diamide-5-hydroxystilbene;
4',5-diamide-3-hydroxystilbene;
3,5,4'-triamide stilbene;
3-amino-5,4'-dihydroxystilbene;
5-amino-3,4'-dihydroxystilbene;
4'-amino-3,5-dihydroxystilbene;
3,5-diamino-4'-hydroxystilbene;
3,4'-diamino-5-hydroxystilbene;
4',5-diamino-3-hydroxystilbene;
3,5,4'-triamino stilbene;
3-imino-5,4'-dihydroxystilbene;
5-imino-3,4'-dihydroxystilbene;
4'-imino-3,5-dihydroxystilbene;
3,5-diimino-4'-hydroxystilbene;
3,4'-diimino-5-hydroxystilbene;
4',5-diimino-3-hydroxystilbene;
3,5,4'-triimino stilbene;
3-amidino-5,4'-dihydroxystilbene;
5-amidino-3,4'-dihydroxystilbene;
4'-amidino-3,5-dihydroxystilbene;
3,5-diamidino-4'-hydroxystilbene;
3,4'-diamidino-5-hydroxystilbene;
4',5-diamidino-3-hydroxystilbene; and
3,5,4'-triamidino stilbene.

II. Linear or Branched Volatile or Near Volatile Silicone

The compositions of the invention comprise at least one linear or branched volatile or linear near volatile silicone in the oil phase of the emulsion. Suggested ranges for the volatile or near volatile linear or branched silicone are from about 0.1 to 90%, preferably from about 0.5 to 85%, more preferably from about 1 to 75% by weight of the total composition. The term "volatile" means that the linear silicone has a vapor pressure of greater than about 2 mm. of mercury at 20° C. The term "near volatile" means that the linear silicone has a vapor pressure ranging from about 1 to about 2 mm. of mercury at 20° C. The linear volatile or near volatile silicones that may be used include those having the general formula:

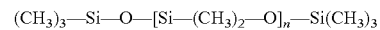

(CH₃)₃—Si—O—[Si—(CH₃)₂—O]ₙ—Si(CH₃)₃ where n=0, 1, 2, 3, 4, 5, 6, 7, or 8; preferably 0, 1, 2, 3, or 4.

Linear volatile silicones are available from various commercial sources including Dow Corning Corporation and General Electric. The Dow Corning volatile silicones are sold under the tradenames Dow Corning 244, 245, 344, and 200 fluids. These fluids include hexamethyldisiloxane (viscosity 0.65 centistokes (abbreviated cst)), octamethyltrisiloxane (1.0 cst), decamethyltetrasiloxane (1.5 cst), dodecamethylpentasiloxane (2 cst) and mixtures thereof, with all viscosity measurements being at 25° C.

Suitable linear branched volatile silicones include methyl trimethicone which is a branched volatile silicone having the general formula:

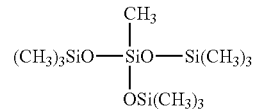

Methyl trimethicone may be purchased from Shin-Etsu Silicones under the tradename TMF-1.5, having a viscosity of 1.5 centistokes at 25° C.

III. Other Ingredients

In addition to the resveratrol derivative and linear volatile or near volatile silicone, the emulsion composition may contain other ingredients such as other oils, humectants, aqueous phase structuring agents, particulates, preservatives, botanical extracts, and the like.

A. Other Oils

In addition to the linear volatile or near volatile silicone, the oil phase may contain one or more cyclic volatile silicone oils, nonvolatile silicone oils, paraffinic hydrocarbons, esters, and the like. The term "nonvolatile" means that the silicone oil has a vapor pressure of less than about 1 mm.

of mercury at 25° C. The silicone oil may be water soluble or water insoluble, but is preferably water insoluble. Suitable ranges include from about 0.01 to 80%, preferably from about 0.1 to 60%, more preferably from about 0.5 to 40% by weight of the total composition.

1. Volatile Cyclic Silicones

Suitable volatile cyclic silicone oils that may be used in the compositions generally have a viscosity ranging from about 0.5 to 3 centistokes 25° C. and include cyclic silicones having the general formula:

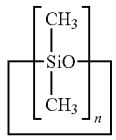

where n=3-6. Examples of such cyclic silicones include octamethylcyclotetrasiloxane, decamethylcyclopentasiloxane, dodecamethylcyclohexasiloxane and the like.

2. Nonvolatile Silicones

Suitable nonvolatile silicones preferably have a viscosity ranging from about 4 to 800,000 cst, preferably 10 to 200,000 cst at 25° C. Suitable silicones include amine functional silicones such as amodimethicone; phenyl substituted silicones such as bisphenylhexamethicone, trimethylsiloxyphenyl dimethicone, phenyl trimethicone, or polyphenylmethylsiloxane; dimethicone, dimethicone substituted with $C_{2-30}$ alkyl groups such cetyl dimethicone, or fluorinated silicones such as trifluoropropyl dimethicone.

Nonvolatile silicones may have the following general formula:

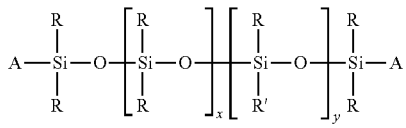

wherein R and R' are each independently $C_{1-30}$ straight or branched chain, saturated or unsaturated alkyl, phenyl or aryl, trialkylsiloxy, and x and y are each independently 0 to 1,000,000; with the proviso that there is at least one of either x or y, and A is alkyl siloxy endcap unit. Preferred is where A is a methyl siloxy endcap unit; in particular trimethylsiloxy, and R and R' are each independently a $C_{1-30}$ straight or branched chain alkyl, phenyl, or trimethylsiloxy, more preferably a $C_{1-22}$ alkyl, phenyl, or trimethylsiloxy, most preferably methyl, phenyl, or trimethylsiloxy, and resulting silicone is dimethicone, phenyl dimethicone, diphenyl dimethicone, phenyl trimethicone, or trimethylsiloxyphenyl dimethicone. Other examples include alkyl dimethicones such as cetyl dimethicone, and the like wherein at least one R is a fatty alkyl ($C_{12}$, $C_{14}$, $C_{16}$, $C_{18}$, $C_{20}$, or $C_{22}$), and the other R is methyl, and A is a trimethylsiloxy endcap unit, provided such alkyl dimethicone is a pourable liquid at room temperature. Phenyl trimethicone can be purchased from Dow Corning Corporation under the tradename 556 Fluid. Trimethylsiloxyphenyl dimethicone can be purchased from Wacker-Chemie under the tradename PDM-1000. Cetyl dimethicone, also referred to as a liquid silicone wax, may be purchased from Dow Corning as Fluid 2502, or from DeGussa Care & Surface Specialties under the tradenames Abil Wax 9801, or 9814.

3. Volatile Paraffinic Hydrocarbons

Also suitable as the volatile oils are various straight or branched chain paraffinic hydrocarbons having 5, 6, 7, 8, 9, 10, 11, 12, 13, 14, 15, 16, 17, 18, 19, or 20 carbon atoms, more preferably 8 to 16 carbon atoms. Suitable hydrocarbons include pentane, hexane, heptane, decane, dodecane, tetradecane, tridecane, and $C_{8-20}$ isoparaffins as disclosed in U.S. Pat. Nos. 3,439,088 and 3,818,105, both of which are hereby incorporated by reference.

Preferred volatile paraffinic hydrocarbons have a molecular weight of 70-225, preferably 160 to 190 and a boiling point range of 30 to 320, preferably 60 to 260° C., and a viscosity of less than about 10 cst. at 25° C. Such paraffinic hydrocarbons are available from EXXON under the ISOPARS trademark, and from the Permethyl Corporation. Suitable $C_{12}$ isoparaffins are manufactured by Permethyl Corporation under the tradename Permethyl 99A. Various $C_{16}$ isoparaffins commercially available, such as isohexadecane (having the tradename Permethyl R), are also suitable.

4. Esters

A variety of nonvolatile oils other than silicones are also suitable for use in the cosmetic compositions of the invention. The nonvolatile oils generally have a viscosity of greater than about 4 to 10 centistokes at 25° C., and may range in viscosity up to about 1,000,000 centipoise at 25° C. Examples of nonvolatile oils include, but are not limited to:

(a). Esters

Suitable esters are mono-, di-, and triesters. The composition may comprise one or more esters selected from the group, or mixtures thereof.

(i) Monoesters

Monoesters are defined as esters formed by the reaction of a monocarboxylic acid having the formula R—COOH, wherein R is a straight or branched chain saturated or unsaturated alkyl having 2 to 45 carbon atoms, or phenyl; and an alcohol having the formula R—OH wherein R is a straight or branched chain saturated or unsaturated alkyl having 2-30 carbon atoms, or phenyl. Both the alcohol and the acid may be substituted with one or more hydroxyl groups. Either one or both of the acid or alcohol may be a "fatty" acid or alcohol, and may have from about 6 to 30 carbon atoms, more preferably 12, 14, 16, 18, or 22 carbon atoms in straight or branched chain, saturated or unsaturated form. Examples of monoester oils that may be used in the compositions of the invention include hexyl laurate, butyl isostearate, hexadecyl isostearate, cetyl palmitate, isostearyl neopentanoate, stearyl heptanoate, isostearyl isononanoate, steary lactate, stearyl octanoate, stearyl stearate, isononyl isononanoate, and so on.

(ii). Diesters

Suitable diesters are the reaction product of a dicarboxylic acid and an aliphatic or aromatic alcohol or an aliphatic or aromatic alcohol having at least two substituted hydroxyl groups and a monocarboxylic acid. The dicarboxylic acid may contain from 2 to 30 carbon atoms, and may be in the straight or branched chain, saturated or unsaturated form. The dicarboxylic acid may be substituted with one or more hydroxyl groups. The aliphatic or aromatic alcohol may also contain 2 to 30 carbon atoms, and may be in the straight or branched chain, saturated, or unsaturated form. Preferably, one or more of the acid or alcohol is a fatty acid or alcohol, i.e. contains 12-22 carbon atoms. The dicarboxylic acid may also be an alpha hydroxy acid. The ester may be in the dimer or trimer form. Examples of diester oils that may be used in the compositions of the invention include diisotearyl malate, neopentyl glycol dioctanoate, dibutyl sebacate, dicetearyl dimer dilinoleate, dicetyl adipate, diisocetyl adipate, diisononyl adipate, diisostearyl dimer dilinoleate, diisostearyl fumarate, diisostearyl malate, dioctyl malate, and so on.

(iii). Triesters

Suitable triesters comprise the reaction product of a tricarboxylic acid and an aliphatic or aromatic alcohol or alternatively the reaction product of an aliphatic or aromatic alcohol having three or more substituted hydroxyl groups with a monocarboxylic acid. As with the mono- and diesters mentioned above, the acid and alcohol contain 2 to 30 carbon atoms, and may be saturated or unsaturated, straight or branched chain, and may be substituted with one or more hydroxyl groups. Preferably, one or more of the acid or alcohol is a fatty acid or alcohol containing 12 to 22 carbon atoms. Examples of triesters include esters of arachidonic, citric, or behenic acids, such as triarachidin, tributyl citrate, triisostearyl citrate, tri $C_{12-13}$ alkyl citrate, tricaprylin, tricaprylyl citrate, tridecyl behenate, trioctyldodecyl citrate, tridecyl behenate; or tridecyl cocoate, tridecyl isononanoate, and so on.

Esters suitable for use in the composition are further described on pages 1670-1676 of the C.T.F.A. Cosmetic Ingredient Dictionary and Handbook, Eighth Edition, 2000, which is hereby incorporated by reference in its entirety.

5. Nonvolatile Hydrocarbons

It may be desirable to incorporate one or more nonvolatile hydrocarbon oils into the composition. Suitable nonvolatile hydrocarbon oils include paraffinic hydrocarbons and olefins, preferably those having greater than about 20 carbon atoms. Examples of such hydrocarbon oils include $C_{24-28}$ olefins, $C_{30-45}$ olefins, $C_{20-40}$ isoparaffins, hydrogenated polyisobutene, polyisobutene, polydecene, hydrogenated polydecene, mineral oil, pentahydrosqualene, squalene, squalane, and mixtures thereof. In one preferred embodiment such hydrocarbons have a molecular weight ranging from about 300 to 1000 Daltons.

6. Glyceryl Esters of Fatty Acids

Synthetic or naturally occurring glyceryl esters of fatty acids, or triglycerides, are also suitable for use in the compositions. Both vegetable and animal sources may be used. Examples of such oils include castor oil, lanolin oil, $C_{10-18}$ triglycerides, caprylic/capric/triglycerides, sweet almond oil, apricot kernel oil, sesame oil, camelina sativa oil, tamanu seed oil, coconut oil, corn oil, cottonseed oil, linseed oil, ink oil, olive oil, palm oil, illipe butter, rapeseed oil, soybean oil, grapeseed oil, sunflower seed oil, walnut oil, and the like.

Also suitable are synthetic or semi-synthetic glyceryl esters, such as fatty acid mono-, di-, and triglycerides which are natural fats or oils that have been modified, for example, mono-, di- or triesters of polyols such as glycerin. In an example, a fatty ($C_{12-22}$) carboxylic acid is reacted with one or more repeating glyceryl groups. glyceryl stearate, diglyceryl diiosostearate, polyglyceryl-3 isostearate, polyglyceryl-4 isostearate, polyglyceryl-6 ricinoleate, glyceryl dioleate, glyceryl diisotearate, glyceryl tetraisostearate, glyceryl trioctanoate, diglyceryl distearate, glyceryl linoleate, glyceryl myristate, glyceryl isostearate, PEG castor oils, PEG glyceryl oleates, PEG glyceryl stearates, PEG glyceryl tallowates, and so on.

7. Fluorinated Oils

Various types of fluorinated oils may also be suitable for use in the compositions including but not limited to fluorinated silicones, fluorinated esters, or perfluropolyethers. Particularly suitable are fluorosilicones such as trimethylsilyl endcapped fluorosilicone oil, polytrifluoropropylmethylsiloxanes, and similar silicones such as those disclosed in U.S. Pat. No. 5,118,496 which is hereby incorporated by reference. Perfluoropolyethers include those disclosed in U.S. Pat. Nos. 5,183,589, 4,803,067, 5,183,588 all of which are hereby incorporated by reference, which are commercially available from Montefluos under the trademark Fomblin.

B. The Aqueous Phase Structuring Agent

The emulsion composition of the invention may also contain at least one aqueous phase structuring agent, that is an agent that increases the viscosity of, or thickens, the aqueous phase of the composition. If present, the aqueous phase structuring agent is compatible with the resveratrol derivative and the other ingredients in the formulation. Suitable ranges are from about 0.01 to 30%, preferably from about 0.1 to 20%, more preferably from about 0.5 to 15% by weight of the total composition. Examples of such agents include various acrylate based thickening agents, natural or synthetic gums, polysaccharides, and the like.

1. Polysaccharides

A variety of polysaccharides may be suitable aqueous phase thickening agents. Examples of such polysaccharides include naturally derived materials such as agar, agarose, alicaligenes polysaccharides, algin, alginic acid, acacia gum, amylopectin, chitin, dextran, cassia gum, cellulose gum, gelatin, gellan gum, hyaluronic acid, hydroxyethyl cellulose, methyl cellulose, ethyl cellulose, pectin, sclerotium gum, xanthan gum, pectin, trehelose, gelatin, and so on.

2. Acrylate Polymers

For example, acrylic polymeric thickeners comprised of monomers A and B wherein A is selected from the group consisting of acrylic acid, methacrylic acid, and mixtures thereof; and B is selected from the group consisting of a $C_{1-22}$ alkyl acrylate, a $C_{1-22}$ alky methacrylate, and mixtures thereof are suitable. In one embodiment the A monomer comprises one or more of acrylic acid or methacrylic acid, and the B monomer is selected from the group consisting of a $C_{1-10}$, most preferably $C_{1-4}$ alkyl acrylate, a $C_{1-10}$, most preferably $C_{1-4}$ alkyl methacrylate, and mixtures thereof. Most preferably the B monomer is one or more of methyl or ethyl acrylate or methacrylate. The acrylic copolymer may be supplied in an aqueous solution having a solids content ranging from about 10-60%, preferably 20-50%, more preferably 25-45% by weight of the polymer, with the remainder water. The composition of the acrylic copolymer may contain from about 0.1-99 parts of the A monomer, and about 0.1-99 parts of the B monomer. Acrylic polymer solutions include those sold by Seppic, Inc., under the tradename Capigel.

Also suitable are acrylic polymeric thickeners that are copolymer of A, B, and C monomers wherein A and B are as defined above, and C has the general formula:

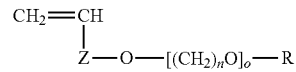

wherein Z is $-(CH_2)_m$; wherein m is 1-10, n is 2-3, o is 2-200, and R is a $C_{10-30}$ straight or branched chain alkyl. Examples of the secondary thickening agent above, are copolymers where A and B are defined as above, and C is CO, and wherein n, o, and R are as above defined. Examples of such secondary thickening agents include acrylates/steareth-20 methacrylate copolymer, which is sold by Rohm & Haas under the tradename Acrysol ICS-1.

Also suitable are acrylate based anionic amphiphilic polymers containing at least one hydrophilic unit and at least one allyl ether unit containing a fatty chain. Preferred are those where the hydrophilic unit contains an ethylenically unsaturated anionic monomer, more specifically a vinyl carboxylic acid such as acrylic acid, methacrylic acid or mixtures thereof, and where the allyl ether unit containing a fatty chain corresponds to the monomer of formula:

$$CH_2=CR'CH_2OB_nR$$

in which R' denotes H or $CH_3$, B denotes the ethylenoxy radical, n is zero or an integer ranging from 1 to 100, R denotes a hydrocarbon radical selected from alkyl, arylalkyl, aryl, alkylaryl and cycloalkyl radicals which contain from 8 to 30 carbon atoms, preferably from 10 to 24, and even more particularly from 12 to 18 carbon atoms. More preferred in this case is where R' denotes H, n is equal to 10 and R denotes a stearyl (C18) radical. Anionic amphiphilic polymers of this type are described and prepared in U.S. Pat. Nos. 4,677,152 and 4,702,844, both of which are hereby incorporated by reference in their entirety. Among these anionic amphiphilic polymers, polymers formed of 20 to 60% by weight acrylic acid and/or methacrylic acid, of 5 to 60% by weight lower alkyl methacrylates, of 2 to 50% by weight allyl ether containing a fatty chain as mentioned above, and of 0 to 1% by weight of a crosslinking agent which is a well-known copolymerizable polyethylenic unsaturated monomer, for instance diallyl phthalate, allyl (meth)acrylate, divinylbenzene, (poly)ethylene glycol dimethacrylate and methylenebisacrylamide. One commercial example of such polymers are crosslinked terpolymers of methacrylic acid, of ethyl acrylate, of polyethylene glycol (having 10 EO units) ether of stearyl alcohol or steareth-10, in particular those sold by the company Allied Colloids under the names SALCARE SC80 and SALCARE SC90, which are aqueous emulsions containing 30% of a crosslinked terpolymer of methacrylic acid, of ethyl acrylate and of steareth-10 allyl ether (40/50/10).

Also suitable are acrylate copolymers such as Polyacrylate-3 which is a copolymer of methacrylic acid, methylmethacrylate, methylstyrene isopropylisocyanate, and PEG-40 behenate monomers; Polyacrylate-10 which is a copolymer of sodium acryloyldimethyltaurate, sodium acrylate, acrylamide and vinyl pyrrolidone monomers; or Polyacrylate-11, which is a copolymer of sodium acryloyldimethylacryloyldimethyl taurate, sodium acrylate, hydroxyethyl acrylate, lauryl acrylate, butyl acrylate, and acrylamide monomers.

Also suitable are crosslinked acrylate based polymers where one or more of the acrylic groups may have substituted long chain alkyl (such as 6-40, 10-30, and the like) groups, for example acrylates/$C_{10-30}$ alkyl acrylate crosspolymer which is a copolymer of C10-30 alkyl acrylate and one or more monomers of acrylic acid, methacrylic acid, or one of their simple esters crosslinked with the allyl ether of sucrose or the allyl ether of pentaerythritol. Such polymers are commonly sold under the Carbopol or Pemulen tradenames and have the CTFA name carbomer.

Particularly suitable as the aqueous phase thickening agent are acrylate based polymeric thickeners sold by Clariant under the Aristoflex trademark such as Aristoflex AVC, which is ammonium acryloyldimethyltaurate/VP copolymer; Aristoflex AVL which is the same polymer has found in AVC dispersed in mixture containing caprylic/capric triglyceride, trilaureth-4, and polyglyceryl-2 sesquiisostearate; or Aristoflex HMB which is ammonium acryloyldimethyltaurate/beheneth-25 methacrylate crosspolymer, and the like.

3. High Molecular Weight PEG or Polyglycerins

Also suitable as the aqueous phase thickening agents are various polyethylene glycols (PEG) derivatives where the degree of polymerization ranges from 1,000 to 200,000. Such ingredients are indicated by the designation "PEG" followed by the degree of polymerization in thousands, such as PEG-45M, which means PEG having 45,000 repeating ethylene oxide units. Examples of suitable PEG derivatives include PEG 2M, 5M, 7M, 9M, 14M, 20M, 23M, 25M, 45M, 65M, 90M, 115M, 160M, 180M, and the like.

Also suitable are polyglycerins which are repeating glycerin moieties where the number of repeating moieties ranges from 15 to 200, preferably from about 20-100. Examples of suitable polyglycerins include those having the CFTA names polyglycerin-20, polyglycerin-40, and the like.

C. Oil Phase Structuring Agents

If desired, the emulsion may contain one or more oil phase structuring agents in the oil phase of the emulsion. The term "oil phase structuring agent" means an ingredient or combination of ingredients, soluble or dispersible in the oil phase, which will increase the viscosity, or structure, the oil phase. The oil phase structuring agent is compatible with the resveratrol derivative and the rest of the formulation ingredients. The term "compatible" means that the oil phase structuring agent and resveratrol derivative are capable of being formulated into a cosmetic product that is generally stable. The structuring agent may be present in an amount sufficient to provide a liquid composition with increased viscosity, a semi-solid, or in some cases a solid composition that may be self-supporting. The structuring agent itself may be present in the liquid, semi-solid, or solid form. Suggested ranges of structuring agent are from about 0.01 to 70%, preferably from about 0.05 to 50%, more preferably from about 0.1-35% by weight of the total composition. Suitable oil phase structuring agents include those that are silicone based or organic based. They may be polymers or non-polymers, synthetic, natural, or a combination of both.

1. Silicone Structuring Agents

A variety of oil phase structuring agents may be silicone based, such as silicone elastomers, silicone gums, silicone waxes, linear silicones having a degree of polymerization that provides the silicone with a degree of viscosity such that when incorporated into the cosmetic composition it is capable of increasing the viscosity of the oil phase. Examples of silicone structuring agents include, but are not limited to:

(a). Silicone Elastomers

Silicone elastomers suitable for use in the compositions of the invention include those that are formed by addition reaction-curing, by reacting an SiH-containing diorganosiloxane and an organopolysiloxane having terminal olefinic unsaturation, or an alpha-omega diene hydrocarbon, in the presence of a platinum metal catalyst. Such elastomers may also be formed by other reaction methods such as condensation-curing organopolysiloxane compositions in the presence of an organotin compound via a dehydrogenation reaction between hydroxyl-terminated diorganopolysiloxane and SiH-containing diorgano-polysiloxane or alpha omega diene; or by condensation-curing organopolysiloxane compositions in the presence of an organotin compound or a titanate ester using a condensation reaction between an hydroxyl-terminated diorganopolysiloxane and a hydrolysable organosiloxane; peroxide-curing organopolysiloxane compositions which thermally cure in the presence of an organoperoxide catalyst.

One type of elastomer that may be suitable is prepared by addition reaction-curing an organopolysiloxane having at least 2 lower alkenyl groups in each molecule or an alpha-omega diene; and an organopolysiloxane having at least 2 silicon-bonded hydrogen atoms in each molecule; and a platinum-type catalyst. While the lower alkenyl groups such as vinyl, can be present at any position in the molecule, terminal olefinic unsaturation on one or both molecular terminals is preferred. The molecular structure of this component may be straight chain, branched straight chain, cyclic, or network. These organopolysiloxanes are exemplified by methylvinylsiloxanes, methylvinylsiloxane-dimethylsiloxane copolymers, dimethylvinylsiloxy-terminated dimethylpolysiloxanes, dimethylvinylsiloxy-terminated dimethylsiloxane-methylphenylsiloxane copolymers, dimethylvinylsiloxy-terminated dimethylsiloxane-diphenylsiloxane-methylvinylsiloxane copolymers, trimethylsiloxy-terminated dimethylsiloxane-methylvinylsiloxane copolymers, trimethylsiloxy-terminated dimethylsiloxane-methylphenylsiloxane-methylvinylsiloxane copolymers, dimethylvinylsiloxy-terminated methyl(3,3,3-trifluoropropyl) polysiloxanes, and dimethylvinylsiloxy-terminated dimethylsiloxane-methyl(3,3,-trifluoropropyl)siloxane copolymers, decadiene, octadiene, heptadiene, hexadiene, pentadiene, or tetradiene, or tridiene.

Curing proceeds by the addition reaction of the silicon-bonded hydrogen atoms in the dimethyl methylhydrogen siloxane, with the siloxane or alpha-omega diene under catalysis using the catalyst mentioned herein. To form a highly crosslinked structure, the methyl hydrogen siloxane must contain at least 2 silicon-bonded hydrogen atoms in each molecule in order to optimize function as a crosslinker.

The catalyst used in the addition reaction of silicon-bonded hydrogen atoms and alkenyl groups, and is concretely exemplified by chloroplatinic acid, possibly dissolved in an alcohol or ketone and this solution optionally aged, chloroplatinic acid-olefin complexes, chloroplatinic acid-alkenylsiloxane complexes, chloroplatinic acid-diketone complexes, platinum black, and carrier-supported platinum.

Examples of suitable silicone elastomers for use in the compositions of the invention may be in the powder form, or dispersed or solubilized in solvents such as volatile or non-volatile silicones, or silicone compatible vehicles such as paraffinic hydrocarbons or esters. Examples of silicone elastomer powders include vinyl dimethicone/methicone silesquioxane crosspolymers like Shin-Etsu's KSP-100, KSP-101, KSP-102, KSP-103, KSP-104, KSP-105, hybrid silicone powders that contain a fluoroalkyl group like Shin-Etsu's KSP-200 which is a fluoro-silicone elastomer, and hybrid silicone powders that contain a phenyl group such as Shin-Etsu's KSP-300, which is a phenyl substituted silicone elastomer; and Dow Corning's DC 9506. Examples of silicone elastomer powders dispersed in a silicone compatible vehicle include dimethicone/vinyl dimethicone crosspolymers supplied by a variety of suppliers including Dow Corning Corporation under the tradenames 9040 or 9041, GE Silicones under the tradename SFE 839, or Shin-Etsu Silicones under the tradenames KSG-15, 16, 18. KSG-15 has the CTFA name cyclopentasiloxane/dimethicone/vinyl dimethicone crosspolymer. KSG-18 has the INCI name phenyl trimethicone/dimethicone/phenyl vinyl dimethicone crossoplymer. Silicone elastomers may also be purchased from Grant Industries under the Gransil trademark. Also suitable are silicone elastomers having long chain alkyl substitutions such as lauryl dimethicone/vinyl dimethicone crosspolymers supplied by Shin Etsu under the tradenames KSG-31, KSG-32, KSG-41, KSG-42, KSG-43, and KSG-44. Cross-linked organopolysiloxane elastomers useful in the present invention and processes for making them are further described in U.S. Pat. No. 4,970,252 to Sakuta et al., issued Nov. 13, 1990; U.S. Pat. No. 5,760,116 to Kilgour et al., issued Jun. 2, 1998; U.S. Pat. No. 5,654,362 to Schulz, Jr. et al. issued Aug. 5, 1997; and Japanese Patent Application JP 61-18708, assigned to Pola Kasei Kogyo KK, each of which are herein incorporated by reference in its entirety.

(b). Silicone Gums

Also suitable for use as an oil phase structuring agent are one or more silicone gums. The term "gum" means a silicone polymer having a degree of polymerization sufficient to provide a silicone having a gum-like texture. In certain cases the silicone polymer forming the gum may be crosslinked. The silicone gum typically has a viscosity ranging from about 500,000 to 100 million cst at 25° C., preferably from about 600,000 to 20 million, more preferably from about 600,000 to 12 million cst. All ranges mentioned herein include all subranges, e.g. 550,000; 925,000; 3.5 million.

The silicone gums that are used in the compositions include, but are not limited to, those of the general formula wherein:

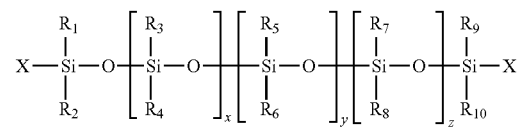

$R_1$ to $R_9$ are each independently an alkyl having 1 to 30 carbon atoms, aryl, or aralkyl; and X is OH or a $C_{1-30}$ alkyl, or vinyl; and wherein x, y, or z may be zero with the proviso that no more than two of x, y, or z are zero at any one time, and further that x, y, and z are such that the silicone gum has a viscosity of at least about 500,000 cst, ranging up to about 100 million centistokes at 25° C. Preferred is where R is methyl or OH.

Such silicone gums may be purchased in pure form from a variety of silicone manufacturers including Wacker-Chemie or Dow Corning, and the like. Such silicone gums include those sold by Wacker-Belsil under the trade names CM3092, Wacker-Belsil 1000, or Wacker-Belsil DM 3096. A silicone gum where X is OH, also referred to as dimethiconol, is available from Dow Corning Corporation under the trade name 1401. The silicone gum may also be purchased in the form of a solution or dispersion in a silicone compatible vehicle such as volatile or nonvolatile silicone. An example of such a mixture may be purchased from Barnet Silicones under the HL-88 tradename, having the INCI name dimethicone.

(c). Silicone Waxes

Another type of oily phase structuring agent includes silicone waxes that are typically referred to as alkyl silicone waxes which are semi-solids or solids at room temperature. The term "alkyl silicone wax" means a polydimethylsiloxane having a substituted long chain alkyl (such as C16 to 30) that confers a semi-solid or solid property to the siloxane. Examples of such silicone waxes include stearyl dimethicone, which may be purchased from DeGussa Care & Surface Specialties under the tradename Abil Wax 9800 or from Dow Corning under the tradename 2503. Another example is bis-stearyl dimethicone, which may be purchased from Gransil Industries under the tradename Gransil A-18, or behenyl dimethicone, behenoxy dimethicone.

2. Polyamides or Silicone Polyamides

Also suitable as oil phase structuring agents are various types of polymeric compounds such as polyamides or silicone polyamides.

The term silicone polyamide means a polymer comprised of silicone monomers and monomers containing amide groups as further described herein. The silicone polyamide preferably comprises moieties of the general formula:

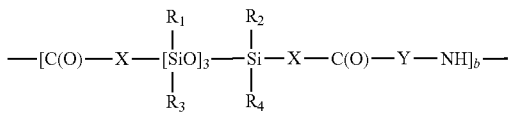

X is a linear or branched alkylene having from about 1-30 carbon atoms;
$R_1$, $R_2$, $R_3$, and $R_4$ are each independently $C_{1-30}$ straight or branched chain alkyl which may be substituted with one or more hydroxyl or halogen groups; phenyl which may be substituted with one or more $C_{1-30}$ alkyl groups, halogen, hydroxyl, or alkoxy groups; or a siloxane chain having the general formula:

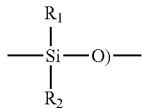

and Y is:
(a) a linear or branched alkylene having from about 1-40 carbon atoms which may be substituted with (i) one or more amide groups having the general formula $R_1CONR_1$, or (ii) $C_{5-6}$ cyclic ring, or (iii) phenylene which may be substituted with one or more $C_{1-10}$ alkyl groups, or (iv) hydroxy, or (v) $C_{3-8}$ cycloalkane, or (vi) $C_{1-20}$ alkyl which may be substituted with one or more hydroxy groups, or (vii) $C_{1-10}$ alkyl amines; or
(b) $TR_5R_6R_7$
wherein $R_5$, $R_6$, and $R_7$, are each independently a $C_{1-10}$ linear or branched alkylenes, and T is $CR_8$ wherein $R_8$ is hydrogen, a trivalent atom N, P, or Al, or a $C_{1-30}$ straight or branched chain alkyl which may be substituted with one or more hydroxyl or halogen groups; phenyl which may be substituted with one or more $C_{1-30}$ alkyl groups, halogen, hydroxyl, or alkoxy groups; or a siloxane chain having the general formula:

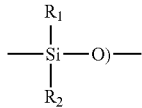

Preferred is where $R_1$, $R_2$, $R_3$, and $R_4$ are $C_{1-10}$, preferably methyl; and X and Y is a linear or branched alkylene. Preferred are silicone polyamides having the general formula:

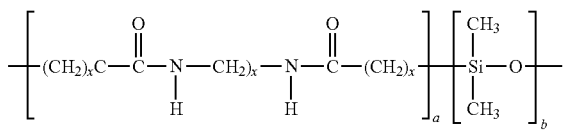

wherein a and b are each independently sufficient to provide a silicone polyamide polymer having a melting point ranging from about 60 to 120° C., and a molecular weight ranging from about 40,000 to 500,000 Daltons. One type of silicone polyamide that may be used in the compositions of the invention may be purchased from Dow Corning Corporation under the tradename Dow Corning 2-8178 gellant which has the CTFA name nylon-611/dimethicone copolymer which is sold in a composition containing PPG-3 myristyl ether.

Also suitable are polyamides such as those purchased from Arizona Chemical under the tradenames Uniclear and Sylvaclear. Such polyamides may be ester terminated or amide terminated. Examples of ester terminated polyamides include, but are not limited to those having the general formula:

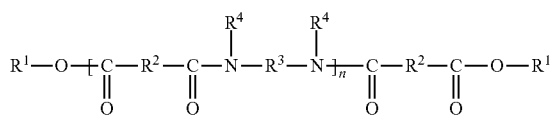

wherein n denotes a number of amide units such that the number of ester groups ranges from about 10% to 50% of the total number of ester and amide groups; each $R_1$ is independently an alkyl or alkenyl group containing at least 4 carbon atoms; each $R_2$ is independently a $C_{4-42}$ hydrocarbon group, with the proviso that at least 50% of the $R_2$ groups are a C30-42 hydrocarbon; each $R_3$ is independently an organic group containing at least 2 carbon atoms, hydrogen atoms and optionally one or more oxygen or nitrogen atoms; and each $R_4$ is independently a hydrogen atom, a $C_{1-10}$ alkyl group or a direct bond to $R_3$ or to another $R_4$, such that the nitrogen atom to which $R_3$ and $R_4$ are both attached forms part of a heterocyclic structure defined by $R_4$—N—$R_3$, with at least 50% of the groups $R_4$ representing a hydrogen atom.

General examples of ester and amide terminated polyamides that may be used as oil phase gelling agents include those sold by Arizona Chemical under the tradenames Sylvaclear A200V or A2614V, both having the CTFA name ethylenediamine/hydrogenated dimer dilinoleate copolymer/bis-di-$C_{14-18}$ alkyl amide; Sylvaclear AF1900V; Sylvaclear C75V having the CTFA name bis-stearyl ethylenediamine/neopentyl glycol/stearyl hydrogenated dimer dilinoleate copolymer; Sylvaclear PA1200V having the CTFA name Polyamide-3; Sylvaclear PE400V; Sylvaclear WF1500V; or Uniclear, such as Uniclear 100VG having the INCI name ethylenediamine/stearyl dimer dilinoleate copolymer; or ethylenediamine/stearyl dimer ditallate copolymer. Other examples of suitable polyamides include those sold by Henkel under the Versamid trademark (such as Versamid 930, 744, 1655), or by Olin Mathieson Chemical Corp. under the brand name Onamid S or Onamid C.

3. Natural or Synthetic Organic Waxes

Also suitable as the oil phase structuring agent may be one or more natural or synthetic waxes such as animal, vegetable, or mineral waxes. Preferably such waxes will have a higher melting point such as from about 60 to 150° C., more preferably from about 65 to 100° C. Examples of such waxes include waxes made by Fischer-Tropsch synthesis, such as polyethylene or synthetic wax; or various vegetable waxes such as bayberry, candelilla, ozokerite, acacia, beeswax, ceresin, cetyl esters, flower wax, citrus wax, carnauba wax, jojoba wax, japan wax, polyethylene, microcrystalline, rice bran, lanolin wax, mink, montan, bayberry, ouricury, ozokerite, palm kernel wax, paraffin, avocado wax, apple wax, shellac wax, clary wax, spent grain wax, grape wax, and polyalkylene glycol derivatives thereof such as PEG6-20 beeswax, or PEG-12 carnauba wax; or fatty acids or fatty alcohols, including esters thereof, such as hydroxystearic acids (for example 12-hydroxy stearic acid), tristearin, tribehenin, and so on.

4. Montmorillonite Minerals

One type of structuring agent that may be used in the composition comprises natural or synthetic montmorillonite minerals such as hectorite, bentonite, and quaternized derivatives thereof, which are obtained by reacting the minerals with a quaternary ammonium compound, such as stearalkonium bentonite, hectorites, quaternized hectorites such as Quaternium-18 hectorite, attapulgite, carbonates such as propylene carbonate, bentones, and the like.

5. Silicas and Silicates

Another type of structuring agent that may be used in the oil phase of the composition is silica, silicates, or silica silylate, and alkali metal or alkaline earth metal derivatives thereof. These silicas and silicates are generally found in the particulate form and include silica, silica silylate, magnesium aluminum silicate, and the like.

D. Surfactants

The composition may contain one or more surfactants, which may be silicone or organic. The surfactants will aid in the formation of stable emulsions of either the water-in-oil or oil-in-water form. If present, the surfactant may range from about 0.001 to 30%, preferably from about 0.005 to 25%, more preferably from about 0.1 to 20% by weight of the total composition.

1. Silicone Surfactants

Suitable silicone surfactants include polyorganosiloxane polymers that have amphiphilic properties, for example contain hydrophilic radicals and lipophilic radicals. These silicone surfactants may be liquids or solids at room temperature.

(a). Dimethicone Copolyols or Alkyl Dimethicone Copolyols

One type of silicone surfactant that may be used is generally referred to as dimethicone copolyol or alkyl dimethicone copolyol. This surfactant is either a water-in-oil or oil-in-water surfactant having an Hydrophile/Lipophile Balance (HLB) ranging from about 2 to 18. Preferably the silicone surfactant is a nonionic surfactant having an HLB ranging from about 2 to 12, preferably about 2 to 10, most preferably about 4 to 6. The term "hydrophilic radical" means a radical that, when substituted onto the organosiloxane polymer backbone, confers hydrophilic properties to the substituted portion of the polymer. Examples of radicals that will confer hydrophilicity are hydroxy-polyethyleneoxy, hydroxyl, carboxylates, and mixtures thereof. The term "lipophilic radical" means an organic radical that, when substituted onto the organosiloxane polymer backbone, confers lipophilic properties to the substituted portion of the polymer. Examples of organic radicals that will confer lipophilicity are $C_{1-40}$ straight or branched chain alkyl, fluoro, aryl, aryloxy, $C_{1-40}$ hydrocarbyl acyl, hydroxy-polypropyleneoxy, or mixtures thereof One type of suitable silicone surfactant has the general formula:

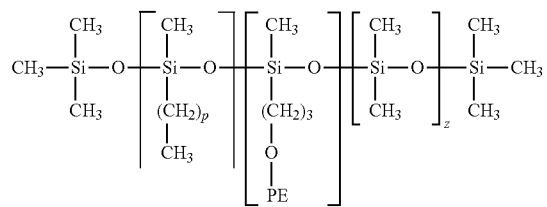

wherein p is 0-40 (the range including all numbers between and subranges such as 2, 3, 4, 13, 14, 15, 16, 17, 18, etc.), and PE is $(-C_2H_4O)_a-(-C_3H_6O)_b-H$ wherein a is 0 to 25, b is 0-25 with the proviso that both a and b cannot be 0 simultaneously, x and y are each independently ranging from 0 to 1 million with the proviso that they both cannot be 0 simultaneously. In one preferred embodiment, x, y, z, a, and b are such that the molecular weight of the polymer ranges from about 5,000 to about 500,000, more preferably from about 10,000 to 100,000, and is most preferably approximately about 50,000 and the polymer is generically referred to as dimethicone copolyol.

One type of silicone surfactant is wherein p is such that the long chain alkyl is cetyl or lauryl, and the surfactant is called, generically, cetyl dimethicone copolyol or lauryl dimethicone copolyol respectively.

In some cases the number of repeating ethylene oxide or propylene oxide units in the polymer are also specified, such as a dimethicone copolyol that is also referred to as PEG-15/PPG-10 dimethicone, which refers to a dimethicone having substituents containing 15 ethylene glycol units and 10 propylene glycol units on the siloxane backbone. It is also possible for one or more of the methyl groups in the above general structure to be substituted with a longer chain alkyl (e.g. ethyl, propyl, butyl, etc.) or an ether such as methyl ether, ethyl ether, propyl ether, butyl ether, and the like.

Examples of silicone surfactants are those sold by Dow Corning under the tradename Dow Corning 3225C Formulation Aid having the CTFA name cyclotetrasiloxane (and) cyclopentasiloxane (and) PEG/PPG-18 dimethicone; or 5225C Formulation Aid, having the CTFA name cyclopentasiloxane (and) PEG/PPG-18/18 dimethicone; or Dow Corning 190 Surfactant having the CTFA name PEG/PPG-18/18 dimethicone; or Dow Corning 193 Fluid, Dow Corning 5200 having the CTFA name lauryl PEG/PPG-18/18 methicone; or Abil EM 90 having the CTFA name cetyl PEG/PPG-14/14 dimethicone sold by Goldschmidt; or Abil EM 97 having the CTFA name bis-cetyl PEG/PPG-14/14 dimethicone sold by Goldschmidt; or Abil WE 09 having the CTFA name cetyl PEG/PPG-10/1 dimethicone in a mixture also containing polyglyceryl-4 isostearate and hexyl laurate; or KF-6011 sold by Shin-Etsu Silicones having the CTFA name PEG-11 methyl ether dimethicone; KF-6012 sold by Shin-Etsu Silicones having the CTFA name PEG/PPG-20/22 butyl ether dimethicone; or KF-6013 sold by Shin-Etsu Silicones having the CTFA name PEG-9 dimethicone; or KF-6015 sold by Shin-Etsu Silicones having the CTFA name PEG-3 dimethicone; or KF-6016 sold by Shin-Etsu Silicones having the CTFA name PEG-9 methyl ether dimethicone; or KF-6017 sold by Shin-Etsu Silicones having the CTFA name PEG-10 dimethicone; or KF-6038 sold by Shin-Etsu Silicones having the CTFA name lauryl PEG-9 polydimethylsiloxyethyl dimethicone.

(b). Crosslinked Silicone Surfactants

Also suitable are various types of crosslinked silicone surfactants are referred to as emulsifying elastomers. They are typically prepared as set forth above with respect to the section "silicone elastomers" except that the silicone elastomers will contain at least one hydrophilic moiety such as polyoxyalkylenated groups. Typically these polyoxyalkylenated silicone elastomers are crosslinked organopolysiloxanes that may be obtained by a crosslinking addition reaction of diorganopolysiloxane comprising at least one hydrogen bonded to silicon and of a polyoxyalkylene comprising at least two ethylenically unsaturated groups. In at least one embodiment, the polyoxyalkylenated crosslinked organopolysiloxanes are obtained by a crosslinking addition reaction of a diorganopolysiloxane comprising at least two hydrogens each bonded to a silicon, and a polyoxyalkylene comprising at least two ethylenically unsaturated groups, optionally in the presence of a platinum catalyst, as described, for example, in U.S. Pat. No. 5,236,986 and U.S. Pat. No. 5,412,004, U.S. Pat. No. 5,837,793 and U.S. Pat. No. 5,811,487, the contents of which are incorporated by reference.

Polyoxyalkylenated silicone elastomers that may be used in at least one embodiment of the invention include those sold by Shin-Etsu Silicones under the names KSG-21, KSG-20, KSG-30, KSG-31, KSG-32, KSG-33; KSG-210 which is dimethicone/PEG-10/15 crosspolymer dispersed in dimethicone; KSG-310 which is PEG-15 lauryl dimethicone crosspolymer; KSG-320 which is PEG-15 lauryl dimethicone crosspolymer dispersed in isododecane; KSG-330 (the former dispersed in triethylhexanoin), KSG-340 which is a mixture of PEG-10 lauryl dimethicone crosspolymer and PEG-15 lauryl dimethicone crosspolymer.

Also suitable are polyglycerolated silicone elastomers like those disclosed in PCT/WO 2004/024798, which is hereby incorporated by reference in its entirety. Such elastomers include Shin-Etsu's KSG series, such as KSG-710 which is dimethicone/polyglycerin-3 crosspolymer dispersed in dimethicone; or lauryl dimethicone/polyglycerin-3 crosspolymer dispersed in a variety of solvent such as isododecane, dimethicone, triethylhexanoin, sold under the Shin-Etsu tradenames KSG-810, KSG-820, KSG-830, or KSG-840. Also suitable are silicones sold by Dow Corning under the tradenames 9010 and DC9011.

One preferred crosslinked silicone elastomer emulsifier is dimethicone/PEG-10/15 crosspolymer.

2. Organic Nonionic Surfactants

The composition may comprise one or more nonionic organic surfactants. Suitable nonionic surfactants include alkoxylated alcohols, or ethers, formed by the reaction of an alcohol with an alkylene oxide, usually ethylene or propylene oxide. Preferably the alcohol is either a fatty alcohol having 6 to 30 carbon atoms Examples of such ingredients include Steareth 2-100, which is formed by the reaction of stearyl alcohol and ethylene oxide and the number of ethylene oxide units ranges from 2 to 100; Beheneth 5-30 which is formed by the reaction of behenyl alcohol and ethylene oxide where the number of repeating ethylene oxide units is 5 to 30; Ceteareth 2-100, formed by the reaction of a mixture of cetyl and stearyl alcohol with ethylene oxide, where the number of repeating ethylene oxide units in the molecule is 2 to 100; Ceteth 1-45 which is formed by the reaction of cetyl alcohol and ethylene oxide, and the number of repeating ethylene oxide units is 1 to 45, and so on.

Other alkoxylated alcohols are formed by the reaction of fatty acids and mono-, di- or polyhydric alcohols with an alkylene oxide. For example, the reaction products of $C_{6-30}$ fatty carboxylic acids and polyhydric alcohols which are monosaccharides such as glucose, galactose, methyl glucose, and the like, with an alkoxylated alcohol. Examples include polymeric alkylene glycols reacted with glyceryl fatty acid esters such as PEG glyceryl oleates, PEG glyceryl stearate; or PEG polyhydroxyalkanotes such as PEG dipolyhydroxystearate wherein the number of repeating ethylene glycol units ranges from 3 to 1000.

Also suitable as nonionic surfactants are formed by the reaction of a carboxylic acid with an alkylene oxide or with a polymeric ether. The resulting products have the general formula: where RCO is the carboxylic ester radical, X is hydrogen or lower alkyl, and n is the number of polymerized alkoxy groups. In the case of the diesters, the two RCO-groups do not need to be identical. Preferably, R is a $C_{6-30}$ straight or branched chain, saturated or unsaturated alkyl, and n is from 1-100.

Monomeric, homopolymeric, or block copolymeric ethers are also suitable as nonionic surfactants. Typically, such ethers are formed by the polymerization of monomeric alkylene oxides, generally ethylene or propylene oxide. Such polymeric ethers have the following general formula: wherein R is H or lower alkyl and n is the number of repeating monomer units, and ranges from 1 to 500.

Other suitable nonionic surfactants include alkoxylated sorbitan and alkoxylated sorbitan derivatives. For example, alkoxylation, in particular ethoxylation of sorbitan provides polyalkoxylated sorbitan derivatives. Esterification of polyalkoxylated sorbitan provides sorbitan esters such as the polysorbates. For example, the polyalkyoxylated sorbitan can be esterified with $C_{6-30}$, preferably $C_{12-22}$ fatty acids. Examples of such ingredients include Polysorbates 20-85, sorbitan oleate, sorbitan sesquioleate, sorbitan palmitate, sorbitan sesquiisostearate, sorbitan stearate, and so on.

Certain types of amphoteric, zwitterionic, or cationic surfactants may also be used in the compositions. Descriptions of such surfactants are set forth in U.S. Pat. No. 5,843,193, which is hereby incorporated by reference in its entirety.

E. Humectants

It may also be desirable to include one or more humectants in the composition. If present, such humectants may range from about 0.001 to 25%, preferably from about 0.005 to 20%, more preferably from about 0.1 to 15% by weight of the total composition. Examples of suitable humectants include glycols, sugars, and the like. Suitable glycols are in monomeric or polymeric form and include polyethylene and polypropylene glycols such as PEG 4-200, which are polyethylene glycols having from 4 to 200 repeating ethylene oxide units; as well as $C_{1-6}$ alkylene glycols such as propylene glycol, butylene glycol, pentylene glycol, and the like. Suitable sugars, some of which are also polyhydric alcohols, are also suitable humectants. Examples of such sugars include glucose, fructose, honey, hydrogenated honey, inositol, maltose, mannitol, maltitol, sorbitol, sucrose, xylitol, xylose, and so on. Preferably, the humectants used in the composition of the invention are $C_{1-6}$, preferably $C_{2-4}$ alkylene glycols, most particularly butylene glycol.

F. Botanical Extracts

It may be desirable to include one or more botanical extracts in the compositions. If so, suggested ranges are from about 0.0001 to 10%, preferably about 0.0005 to 8%, more preferably about 0.001 to 5% by weight of the total composition. Suitable botanical extracts include extracts from plants (herbs, roots, flowers, fruits, seeds) such as flowers, fruits, vegetables, and so on, including yeast ferment extract, padica pavonica extract, thermus thermophilis ferment extract, camelina sativa seed oil, boswellia serrata extract, olive extract, aribodopsis thaliana extract, acacia dealbata extract, acer saccharinum (sugar maple), acidopholus, acorus, aesculus, agaricus, agave, agrimonia, algae, aloe, citrus, brassica, cinnamon, orange, apple, blueberry, cranberry, peach, pear, lemon, lime, pea, seaweed, caffeine, green tea, chamomile, willowbark, mulberry, poppy, and those set forth on pages 1646 through 1660 of the CTFA Cosmetic Ingredient Handbook, Eighth Edition, Volume 2. Further specific examples include, but are not limited to, *Glycyrrhiza Glabra, Salix Nigra, Macrocycstis Pyrifera, Pyrus Malus, Saxifraga Sarmentosa, Vilis Vinifera, Morus*

*Nigra, Scutellaria Baicalensis, Anthemis Nobilis, Salvia Sclarea, Rosmarinus Officianalis, Citrus Medica Limonum, Panax Ginseng,* and mixtures thereof.

G. Sunscreens

It may also be desirable to include one or more sunscreens in the compositions of the invention. Such sunscreens include chemical UVA or UVB sunscreens or physical sunscreens in the particulate form.

1. UVA Chemical Sunscreens

If desired, the composition may comprise one or more UVA sunscreens. The term "UVA sunscreen" means a chemical compound that blocks UV radiation in the wavelength range of about 320 to 400 nm. Preferred UVA sunscreens are dibenzoylmethane compounds having the general formula:

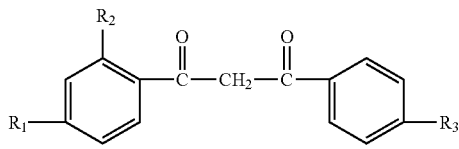

wherein $R_1$ is H, OR and NRR wherein each R is independently H, $C_{1-20}$ straight or branched chain alkyl; $R_2$ is H or OH; and $R_3$ is H, $C_{1-20}$ straight or branched chain alkyl.

Preferred is where $R_1$ is OR where R is a $C_{1-20}$ straight or branched alkyl, preferably methyl; $R_2$ is H; and $R_3$ is a $C_{1-20}$ straight or branched chain alkyl, more preferably, butyl.

Examples of suitable UVA sunscreen compounds of this general formula include 4-methyldibenzoylmethane, 2-methyldibenzoylmethane, 4-isopropyldibenzoylmethane, 4-tert-butyldibenzoylmethane, 2,4-dimethyldibenzoylmethane, 2,5-dimethyldibenzoylmethane, 4,4'diisopropylbenzoylmethane, 4-tert-butyl-4'-methoxydibenzoylmethane, 4,4'-diisopropylbenzoylmethane, 2-methyl-5-isopropyl-4'-methoxydibenzoymethane, 2-methyl-5-tert-butyl-4'-methoxydibenzoylmethane, and so on. Particularly preferred is 4-tert-butyl-4'-methoxydibenzoylmethane, also referred to as Avobenzone. Avobenzone is commercial available from Givaudan-Roure under the trademark Parsol 1789, and Merck & Co. under the tradename Eusolex 9020.

The composition may contain from about 0.001-20%, preferably 0.005-5%, more preferably about 0.005-3% by weight of the composition of UVA sunscreen. In the preferred embodiment of the invention the UVA sunscreen is Avobenzone, and it is present at not greater than about 3% by weight of the total composition.

2. UVB Chemical Sunscreens

The term "UVB sunscreen" means a compound that blocks UV radiation in the wavelength range of from about 290 to 320 nm. A variety of UVB chemical sunscreens exist including alpha-cyano-beta,beta-diphenyl acrylic acid esters as set forth in U.S. Pat. No. 3,215,724, which is hereby incorporated by reference in its entirety. One particular example of an alpha-cyano-beta,beta-diphenyl acrylic acid ester is Octocrylene, which is 2-ethylhexyl 2-cyano-3,3-diphenylacrylate. In certain cases the composition may contain no more than about 110% by weight of the total composition of octocrylene. Suitable amounts range from about 0.001-10% by weight. Octocrylene may be purchased from BASF under the tradename Uvinul N-539.

Other suitable sunscreens include benzylidene camphor derivatives as set forth in U.S. Pat. No. 3,781,417, which is hereby incorporated by reference in its entirety. Such benzylidene camphor derivatives have the general formula:

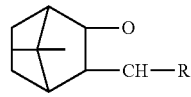

wherein R is p-tolyl or styryl, preferably styryl. Particularly preferred is 4-methylbenzylidene camphor, which is a lipid soluble UVB sunscreen compound sold under the tradename Eusolex 6300 by Merck.

Also suitable are cinnamate derivatives having the general formula:

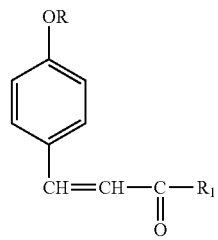

wherein R and $R_1$ are each independently a $C_{1-20}$ straight or branched chain alkyl. Preferred is where R is methyl and $R_1$ is a branched chain $C_{1-10}$, preferably $C_8$ alkyl. The preferred compound is ethylhexyl methoxycinnamate, also referred to as Octoxinate or octyl methoxycinnamate. The compound may be purchased from Givaudan Corporation under the tradename Parsol MCX, or BASF under the tradename Uvinul MC 80. Also suitable are mono-, di-, and triethanolamine derivatives of such methoxy cinnamates including diethanolamine methoxycinnamate. Cinoxate, the aromatic ether derivative of the above compound is also acceptable. If present, the Cinoxate should be found at no more than about 3% by weight of the total composition.

Also suitable as UVB screening agents are various benzophenone derivatives having the general formula:

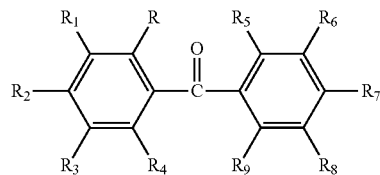

wherein R through $R_9$ are each independently H, OH, $NaO_3S$, $SO_3H$, $SO_3Na$, Cl, R", OR" where R" is $C_{1-20}$ straight or branched chain alkyl Examples of such compounds include Benzophenone 1, 2, 3, 4, 5, 6, 7, 8, 9, 10, 11, and 12. Particularly preferred is where the benzophenone derivative is Benzophenone 3 (also referred to as Oxybenzone), Benzophenone 4 (also referred to as Sulisobenzone), Benzophenone 5 (Sulisobenzone Sodium), and the like. Most preferred is Benzophenone 3.

Also suitable are certain menthyl salicylate derivatives having the general formula:

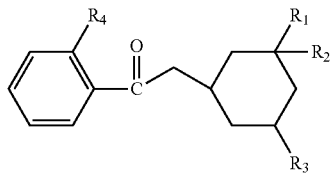

wherein $R_1$, $R_2$, $R_3$, and $R_4$ are each independently H, OH, $NH_2$, or $C_{1-20}$ straight or branched chain alkyl. Particularly preferred is where $R_1$, $R_2$, and $R_3$ are methyl and $R_4$ is hydroxyl or $NH_2$, the compound having the name homomenthyl salicylate (also known as Homosalate) or menthyl anthranilate. Homosalate is available commercially from Merck under the tradename Eusolex HMS and menthyl anthranilate is commercially available from Haarmann & Reimer under the tradename Heliopan. If present, the Homosalate should be found at no more than about 15% by weight of the total composition.

Various amino benzoic acid derivatives are suitable UVB absorbers including those having the general formula:

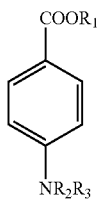

wherein $R_1$, $R_2$, and $R_3$ are each independently H, $C_{1-20}$ straight or branched chain alkyl which may be substituted with one or more hydroxy groups. Particularly preferred is wherein $R_1$ is H or $C_{1-8}$ straight or branched alkyl, and $R_2$ and $R_3$ are H, or $C_{1-8}$ straight or branched chain alkyl. Particularly preferred are PABA, ethyl hexyl dimethyl PABA (Padimate O), ethyldihydroxypropyl PABA, and the like. If present Padimate O should be found at no more than about 8% by weight of the total composition.

Salicylate derivatives are also acceptable UVB absorbers. Such compounds have the general formula: wherein R is a straight or branched chain alkyl, including derivatives of the above compound formed from mono-, di-, or triethanolamines. Particular preferred are octyl salicylate, TEA-salicylate, DEA-salicylate, and mixtures thereof.

Generally, the amount of the UVB chemical sunscreen present may range from about 0.001-45%, preferably 0.005-40%, more preferably about 0.01-35% by weight of the total composition.

If desired, the compositions of the invention may be formulated to have a certain SPF (sun protective factor) values ranging from about 1-50, preferably about 2-45, most preferably about 5-30. Calculation of SPF values is well known in the art. Preferably, the claimed compositions have SPF values greater than 4.

H. Particulate Materials

The compositions of the invention may contain particulate materials in the form of pigments, inert particulates, or mixtures thereof. If present, suggested ranges are from about 0.1-75%, preferably about 0.5-70%, more preferably about 0.1-65% by weight of the total composition. In the case where the composition may comprise mixtures of pigments and powders, suitable ranges include about 0.01-75% pigment and 0.1-75% powder, such weights by weight of the total composition.

1. Powders

The particulate matter may be colored or non-colored (for example white) non-pigmentatious powders. Suitable non-pigmentatious powders include bismuth oxychloride, titanated mica, fumed silica, spherical silica, polymethylmethacrylate, micronized teflon, boron nitride, acrylate copolymers, aluminum silicate, aluminum starch octenylsuccinate, bentonite, calcium silicate, cellulose, chalk, corn starch, diatomaceous earth, fuller's earth, glyceryl starch, hectorite, hydrated silica, kaolin, magnesium aluminum silicate, magnesium trisilicate, maltodextrin, montmorillonite, microcrystalline cellulose, rice starch, silica, talc, mica, titanium dioxide, zinc laurate, zinc myristate, zinc rosinate, alumina, attapulgite, calcium carbonate, calcium silicate, dextran, kaolin, nylon, silica silylate, silk powder, sericite, soy flour, tin oxide, titanium hydroxide, trimagnesium phosphate, walnut shell powder, or mixtures thereof. The above mentioned powders may be surface treated with lecithin, amino acids, mineral oil, silicone, or various other agents either alone or in combination, which coat the powder surface and render the particles more lipophilic in nature.

2. Pigments

The particulate materials may comprise various organic and/or inorganic pigments. The organic pigments are generally various aromatic types including azo, indigoid, triphenylmethane, anthroquinone, and xanthine dyes which are designated as D&C and FD&C blues, browns, greens, oranges, reds, yellows, etc. Organic pigments generally consist of insoluble metallic salts of certified color additives, referred to as the Lakes. Inorganic pigments include iron oxides, ultramarines, chromium, chromium hydroxide colors, and mixtures thereof. Iron oxides of red, blue, yellow, brown, black, and mixtures thereof are suitable.

I. Preservatives

The composition may contain 0.001-8%, preferably 0.01-6%, more preferably 0.05-5% by weight of the total composition of preservatives. A variety of preservatives are suitable, including such as benzoic acid, benzyl alcohol, benzylhemiformal, benzylparaben, 5-bromo-5-nitro-1,3-dioxane, 2-bromo-2-nitropropane-1,3-diol, butyl paraben, phenoxyethanol, methyl paraben, propyl paraben, diazolidinyl urea, biguanide derivatives, calcium benzoate, calcium propionate, caprylyl glycol, biguanide derivatives, phenoxyethanol, captan, chlorhexidine diacetate, chlorhexidine digluconate, chlorhexidine dihydrochloride, chloroacetamide, chlorobutanol, p-chloro-m-cresol, chlorophene, chlorothymol, chloroxylenol, m-cresol, o-cresol, DEDM Hydantoin, DEDM Hydantoin dilaurate, dehydroacetic acid, diazolidinyl urea, dibromopropamidine diisethionate, DMDM Hydantoin, and the like. In one preferred embodiment the composition is free of parabens.

I. Vitamins and Antioxidants

The compositions of the invention, may contain vitamins and/or coenzymes, as well as antioxidants. If so, 0.001-10%, preferably 0.01-8%, more preferably 0.05-5% by weight of the total composition are suggested. Suitable vitamins include ascorbic acid and derivatives thereof, the B vitamins such as thiamine, riboflavin, pyridoxin, and so on, as well as coenzymes such as thiamine pyrophoshate, flavin adenin dinucleotide, folic acid, pyridoxal phosphate, tetrahydrofolic acid, and so on. Also Vitamin A and derivatives thereof are suitable. Examples are Vitamin A palmitate, acetate, or other esters thereof, as well as Vitamin A in the form of beta carotene. Also suitable is Vitamin E and derivatives thereof such as Vitamin E acetate, nicotinate, or other esters thereof. In addition, Vitamins D and K are suitable.

Suitable antioxidants are ingredients which assist in preventing or retarding spoilage. Examples of antioxidants suitable for use in the compositions of the invention are potassium sulfite, sodium bisulfite, sodium erythrobate, sodium metabisulfite, sodium sulfite, propyl gallate, cysteine hydrochloride, butylated hydroxytoluene, butylated hydroxyanisole, and so on.

IV. The Cosmetic Compositions

The emulsion cosmetic compositions containing the resveratrol derivatives may be found in a variety of forms, such as skin creams or lotions, or color cosmetic compositions such as foundation makeup, mascara, lip color, blush, eyeshadow, and the like. The resveratrol derivative may be found in the water phase or the oil phase of the emulsion depending on the type of derivative. For example, certain hydrophilic derivatives such as resveratrol triphosphate, resveratrol trisulfonate, and the like are water soluble and will generally be found in the water phase of the emulsion. Certain other derivatives are lipophilic in nature and will more likely be found in the oil phase of the emulsion.

Typical skin creams or lotions comprise from about 5-98% water, 1-85% oil, and from about 0.1 to 20% of one or more surfactants. Preferably the surfactants are nonionic and may be in the form of silicones or organic nonionic surfactants.

Typical color cosmetic compositions such as foundations, blush, eyeshadow and the like will preferably contain from about 5-98% water, 1-85% oil, and from about 0.1 to 20% of one or more surfactants in addition to from about 0.1 to 65% of particulates that are pigments or a combination of pigments and powders.

Typical mascara compositions generally contain from about 5-98% water, 1-85% oil, and from about 0.1 to 20% surfactant in addition to natural or synthetic polymers that are film forming, such as aqueous dispersions of acrylic copolymers, aqueous dispersions of polyurethane, or silicone resins.

The invention will be further described in connection with the following examples which are set forth for the purposes of illustration only.

Example 1

Skin treatment oil-in-water (1), and oil-in-water-in-silicone oil (2), creams were prepared as follows:

| Ingredient | w/w % 1 | w/w % 2 |
|---|---|---|
| Water | QS | QS |
| Hydroxyethyl urea | 0.50 | |
| Hyaluronic acid | 9.00 | 9.00 |
| Disodium EDTA | 0.12 | |
| Creatine | 0.05 | |
| Sucrose | 0.50 | |
| Caffeine | 0.20 | |
| Caprylyl glycol | 0.40 | 0.28 |
| Caprylic/capric triglyceride/cetyl alcohol/C12-20 acid PEG-8 ester | 4.00 | |
| PEG-100 stearate | 1.20 | |
| C12-20 acid PEG-8 ester | 4.96 | |
| Caprylic/capric triglyceride | 0.55 | |
| Behenyl alcohol | 0.50 | |
| Coco caprylate caprate | 5.10 | |
| Sweet almond oil | 0.10 | |

-continued

| Ingredient | w/w % 1 | w/w % 2 |
|---|---|---|
| Dimethicone, 100 cst. | 2.50 | |
| Dimethicone, 6 cst | | 5.00 |
| Dimethicone (silicone gum/20 cst dimethicone blend) | | 8.00 |
| Dimethicone/polysilicone 11 | | 6.00 |
| Dimethicone/dimethicone PEG-10/15 crosspolymer | | 1.00 |
| Lauryl PEG-9 polydimethylsiloxyethyl dimethicone | | 1.00 |
| Sesame oil | 0.10 | |
| Potassium cetyl phosphate | 0.50 | |
| Apricot kernel oil | 0.10 | |
| Wheat bran extract/olive extract | 0.20 | 0.20 |
| Cholesterol | 0.20 | |
| Linoleic acid | 0.20 | |
| Cholesterol/potassium sulfate | 0.20 | |
| *Theobroma grandiflorum* seed butter | 1.40 | |
| Lauryl PCA | 0.01 | 1.00 |
| Dimethicone (2.0 cst) | 1.50 | 1.50 |
| Phenoxyethanol | 0.70 | 0.60 |
| Water/polyaminopropyl biguanide | 0.40 | |
| Glycerin | 2.00 | |
| Butylene glycol | 1.00 | |
| Hexylene glycol | | 0.05 |
| Mica/titanium dioxide | 1.00 | 0.75 |
| Mica/titanium dioxide/triethoxycaprylyl silane | | 0.50 |
| Pearl powder | 0.001 | |
| Silica | 0.50 | |
| 30% aqueous sodium hydroxide | 0.35 | |
| Trehalose | 0.50 | |
| N-acetyl glucosamine | 1.00 | 1.00 |
| Water/purified *aribodopsis thaliana* extract/lecithin | 0.50 | 1.00 |
| Aqueous solution acetyl hexapeptide-8 | 1.00 | 1.00 |
| Yeast ferment extract | 1.00 | 1.00 |
| Water/lecithin/*micrococcus* lysate | 0.50 | 0.50 |
| Milk protein/lactose/glucose/fructose | 0.50 | 0.50 |
| Saccharide isomerate | 0.50 | |
| Whey protein | 0.50 | 0.560 |
| Water/butylene glycol/lecithin/lauryldimonium hydroxypropyl hydrolyzed soy protein/lecithin/xanthan gum/ascorbyl tocopheryl maleate | 1.00 | 1.00 |
| Glycerin/*padina povonica* extract | 0.10 | 0.10 |
| *Thermus thermophillus* ferment/glycerin | 0.05 | |
| *Camelina sativa* seed oil | 0.05 | |
| Water/gold/hydrolyzed wheat protein | 0.001 | |
| Sorbitol/water/*ascophyllum nodosum* extract/*asparagopsis armata* extract | 0.25 | |
| Butylene glycol | 0.50 | |
| *Boswellia serrata* extract | 0.05 | |
| *Calophyllum inophyllum* (tamanu) seed oil | 0.05 | |
| Fragrance | 0.20 | |
| FD&C yellow No. 5 (1% aqueous solution) | 0.05 | |
| Aminomethyl propanol | | 0.03 |
| Sodim phosphate dibasic (10% aqueous solution) | | 0.75 |
| Citric acid (10% aqueous solution) | | 0.008 |
| Sodium acrylate/sodium acryloyldimethyl taurate copolymer/hydrogenated polydecene/laureth-8 | 1.00 | 1.00 |
| Ammonium acrylodimethyltaurate/VP copolymer | | 0.70 |
| Water/butylene glycol/decarboxy carnosine HCl | | 0.50 |
| Trisodium resveratrol triphosphate | 0.50 | |
| Resveratrol tripalmitate | | 0.50 |

The composition was prepared by combining the water phase and oil phase ingredients separately, then emulsifying to form an emulsion.

Example 2

A water in silicone oil emulsion skin serum was prepared as follows:

| Ingredient | w/w % |
|---|---|
| Dimethicone/dimethicone PEG-10/15 crosspolymer | 4.00 |
| Dimethicone/dimethiconol | 1.00 |

| Ingredient | w/w % |
|---|---|
| Dimethicone, 6 cst. | 6.00 |
| Trisiloxane (1.0 cst) | 16.00 |
| Water | QS |
| Phenoxyethanol | 0.50 |
| Caprylyl glycol/phenoxyethanol/hexylene glycol/iodopropynyl butylcarbamate | 0.50 |
| Water/polyaminobiguanide | 0.20 |
| Trisodium resveratrol triphosphate | 0.50 |
| Butylene glycol | 2.00 |
| Glycerin | 10.00 |
| Ammonium acrylodimethyltaurate/VP copolymer | 0.50 |
| Sodium citrate | 0.50 |

The composition was prepared by combining the oil phase ingredients and water phase ingredients separately, then mixing well to emulsify.

Example 3

Oil-in-water (O/W) and water-in-oil (W/O) emulsion mascaras were prepared as follows:

| Ingredient | O/W w/w % | W/O w/w % |
|---|---|---|
| Ethylenediamine/Stearyl Dimer Tallate Copolymer - Uniclear 100VG, Arizona Chemical | 10.00 | 12.00 |
| PEG-30 Dipolyhydroxystearate | — | 3.00 |
| Sorbitan tristearate | 1.00 | — |
| Glyceryl stearate/PEG-100 stearate | 1.00 | — |
| Stearic acid | 4.00 | 3.00 |
| Cetyl acetate/Acetylated lanolin alcohol | — | 1.00 |
| Dioctyl adipate/octyl stearate/octyl palmitate | 1.00 | — |
| Stearamide MEA stearate | 3.00 | — |
| Glyceryl olivate | — | 0.50 |
| Dioctyl malate | — | 1.00 |
| Dimethicone (1.5 cst) | 2.50 | 2.50 |
| Cyclomethicone | 5.00 | — |
| Isododecane | 11.00 | 38.00 |
| Ethanol | 0.50 | — |
| Water | QS | QS |
| Silica | 1.00 | — |
| Polysorbate 20 | 2.00 | — |
| Acacia gum | 0.25 | — |
| Black iron oxide | 8.00 | 10.00 |
| Polyvinylpyrrolidone | 1.00 | — |
| 4'-5' dihydroxystilbene-3-O-beta-mono-D-glucoside | 0.50 | — |
| Shellac | 2.00 | — |
| Acrylic copolymer solids dispersed in aqueous solution | 5.00 | 7.00 |
| Preservatives | 0.80 | — |

The mascaras were made by combining the oily phase ingredients except for the cyclomethicone and dimethicone and heating to about 90° C. until solids melted. The cyclomethicone and dimethicone were added to the mixture and the heat maintained at about 60° C. The water phase ingredients were combined and heated to about 60° C. and combined with the mixture. The phases were emulsified to form the final mixture.

Example 4

Emulsion foundation makeup compositions were prepared as follows:

| Ingredient | w/w % |
|---|---|
| Cyclomethicone | 16.90 |
| Polysilicone-11 | 5.00 |

| Ingredient | w/w % |
|---|---|
| Cyclomethicone/dimethiconol | 1.00 |
| Dimethicone copolyol | 1.50 |
| Sorbitan sesquioleate | 1.50 |
| Phenyl trimethicone | 10.00 |
| Dimethicone (2.0 cst) | 10.00 |
| Resveratrol tripalmitate | 0.50 |
| Red Iron Oxide treated with methicone | 0.50 |
| Yellow iron oxide treated with methicone | 1.22 |
| Black iron oxide treated with methicone | 0.13 |
| Titanium dioxide coated with methicone | 8.06 |
| Water | QS |
| Butylene glycol | 5.00 |
| Xanthan gum | 0.10 |
| Magnesium sulfate | 1.00 |
| Laureth-7 | 0.25 |

The water, oil and pigment phases were separately prepared by low shear mixing. The phases were combined with high shear blending to form a foundation makeup composition.

While the invention has been described in connection with the preferred embodiment, it is not intended to limit the scope of the invention to the particular form set forth but, on the contrary, it is intended to cover such alternatives, modifications, and equivalents as may be included within the spirit and scope of the invention as defined by the appended claims.

We claim:

1. A compound selected from the group consisting of:
   3-malate-5,4'-dihydroxystilbene;
   4'-malate-3,5-dihydroxystilbene;
   3,5-dimalate-4'-hydroxystilbene;
   3,4'-dimalate-5-hydroxystilbene; and
   3,5,4'-trimalate-stilbene.

2. The compound of claim 1 which is 3-malate-5,4'-dihydroxystilbene.

3. The compound of claim 1 which is 4'-malate-3,5-dihydroxystilbene.

4. The compound of claim 1 which is 3,5-dimalate-4'-hydroxystilbene.

5. The compound of claim 1 which is 3,4'-dimalate-5-hydroxystilbene.

6. The compound of claim 1 which is 3,5,4'-trimalate stilbene.

7. A topical composition comprising a compound selected from the group consisting of:
   3-malate-5,4'-dihydroxystilbene;
   4'-malate-3,5-dihydroxystilbene;
   3,5-dimalate-4'-hydroxystilbene;
   3,4'-dimalate-5-hydroxystilbene; and
   3,5,4'-trimalate stilbene.

8. The composition of claim 7 in the form of a water-in-oil or an oil-in-water emulsion.

9. The composition of claim 7 further comprising a silicone elastomer.

10. The composition of claim 7 further comprising particulates.

11. The composition of claim 7 in the anhydrous form.

12. The composition of claim 7 further comprising at least one botanical extract.

13. The composition of claim 7 further comprising N-acetyl glucosamine.

14. The composition of claim 7 further comprising a UVA or UVB sunscreen.

15. The composition of claim 7 further comprising at least one nonionic organic surfactant.

16. The composition of claim 7 which is a skin cream or lotion, foundation makeup, blush, concealer, eyeshadow, eyeliner, mascara, or lipstick.

17. The composition of claim 7 which is an oil-in-water skin créme or lotion additionally comprising at least one ester.

18. The composition of claim 7 further comprising a linear or cyclic silicone.

* * * * *